US006815074B2

(12) United States Patent
Aguado et al.

(10) Patent No.: US 6,815,074 B2
(45) Date of Patent: Nov. 9, 2004

(54) POLYMERIC MATERIALS FOR MAKING CONTACT LENSES

(75) Inventors: Celeste Aguado, Atlanta, GA (US); Paul Clement Nicolson, Dunwoody, GA (US); Lynn Cook Winterton, Alpharetta, GA (US); Yongxing Qiu, Duluth, GA (US); John Martin Lally, Lilburn, GA (US); Jacalyn Mary Schremmer, Atlanta, GA (US)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 10/153,040

(22) Filed: May 22, 2002

(65) Prior Publication Data

US 2003/0008154 A1 Jan. 9, 2003

Related U.S. Application Data

(60) Provisional application No. 60/337,763, filed on Nov. 8, 2001, and provisional application No. 60/294,512, filed on May 30, 2001.

(51) Int. Cl.⁷ ................................................. B32B 9/04
(52) U.S. Cl. ......................... 428/447; 528/32; 523/106; 523/107; 524/588; 526/279; 540/139; 540/140; 427/2.24; 427/162
(58) Field of Search .................... 428/447; 528/32; 523/106, 107; 524/588; 526/279; 540/139, 140; 427/2.24, 162

(56) References Cited

U.S. PATENT DOCUMENTS

| | | | |
|---|---|---|---|
| 3,228,741 A | 1/1966 | Becker | |
| 3,341,490 A | 9/1967 | Burdick et al. | |
| 3,808,178 A | 4/1974 | Gaylord | 260/86.1 |
| 3,996,187 A | 12/1976 | Travnicek | 260/37 |
| 3,996,189 A | 12/1976 | Travnicek | 260/37 |
| 4,028,295 A | 6/1977 | Loshaek | 260/29.6 |
| 4,109,070 A | 8/1978 | Loshaek et al. | 526/77 |
| 4,111,535 A | 9/1978 | Loshaek et al. | 351/160 |
| 4,136,250 A | 1/1979 | Mueller et al. | 528/29 |
| 4,153,641 A | 5/1979 | Deichert et al. | 260/827 |
| 4,158,089 A | 6/1979 | Loshaek et al. | 526/264 |
| 4,189,546 A | 2/1980 | Deichert et al. | 528/26 |
| RE30,368 E | 8/1980 | Loshaek et al. | 351/160 |
| 4,228,269 A | 10/1980 | Loshaek et al. | 526/346 |
| 4,312,725 A | 1/1982 | Loshaek et al. | 204/159 |
| 4,424,328 A | 1/1984 | Ellis | 526/279 |
| 4,433,125 A | 2/1984 | Ichinobe et al. | 526/279 |
| 4,463,149 A | 7/1984 | Ellis | 526/279 |
| 4,605,712 A | 8/1986 | Mueller et al. | 525/474 |
| 4,652,622 A | 3/1987 | Friends et al. | 526/279 |
| 4,686,267 A | 8/1987 | Ellis et al. | 526/279 |
| 4,711,943 A | 12/1987 | Harvey, III | 526/279 |
| 4,740,533 A | 4/1988 | Su et al. | 523/106 |
| 4,810,764 A | 3/1989 | Friends et al. | 526/245 |
| RE33,477 E | 12/1990 | Loshaek | 526/313 |
| 5,030,669 A * | 7/1991 | Hendrickson et al. | |
| 5,070,169 A | 12/1991 | Robertson et al. | 528/25 |
| 5,070,170 A | 12/1991 | Robertson et al. | 528/25 |
| 5,158,717 A | 10/1992 | Lai | 264/1.1 |
| 5,196,493 A | 3/1993 | Gruber et al. | 526/245 |
| 5,244,799 A | 9/1993 | Anderson | 435/240 |
| 5,260,000 A | 11/1993 | Nandu et al. | 264/2.1 |
| 5,310,779 A | 5/1994 | Lai | 524/588 |
| 5,321,108 A | 6/1994 | Kunzler et al. | 526/242 |
| 5,336,797 A | 8/1994 | Mcgee et al. | 556/419 |
| 5,346,946 A | 9/1994 | Yokoyama et al. | 524/547 |
| 5,352,714 A | 10/1994 | Lai et al. | 523/107 |
| 5,357,013 A | 10/1994 | Bambury et al. | 526/260 |
| 5,364,918 A | 11/1994 | Valint, Jr. et al. | 526/245 |
| 5,374,662 A | 12/1994 | Lai et al. | 522/172 |
| 5,420,324 A | 5/1995 | Lai et al. | 556/419 |
| 5,451,651 A | 9/1995 | Lai | 526/302 |
| 5,539,016 A | 7/1996 | Kunzler et al. | 523/107 |
| 5,610,252 A | 3/1997 | Bambury et al. | 526/279 |
| 5,760,100 A | 6/1998 | Nicolsen et al. | 523/106 |
| 5,945,498 A | 8/1999 | Hopken et al. | 528/42 |
| 5,948,401 A | 9/1999 | Donabedian et al. | 424/78.04 |

FOREIGN PATENT DOCUMENTS

| | | |
|---|---|---|
| EP | 0 330 616 | 8/1989 |
| EP | 0 395 583 | 10/1990 |
| EP | 0 461 270 | 7/1991 |
| EP | 0 584 764 | 3/1994 |
| WO | WO 92/07013 | 4/1992 |
| WO | WO 94/15980 | 7/1994 |
| WO | WO 95/17689 | 6/1995 |
| WO | WO 95/24187 | 9/1995 |
| WO | WO 96/31792 | 10/1996 |
| WO | WO 99/35520 | 7/1999 |
| WO | WO 99/57177 | 11/1999 |
| WO | WO 00/29130 | 5/2000 |

OTHER PUBLICATIONS

International Search Report.

"Extended Wear in Perspective", Noel A. Brennan, MScOptom, PhD, FAAO and M.–L. Chantal Coles, OD, Optometry and Vision Science, vol. 74, No. 8, Aug. 1997.

(List continued on next page.)

Primary Examiner—Kuo-Liang Peng
(74) Attorney, Agent, or Firm—Jian Zhou; Robert Gorman; R. Scott Meece

(57) ABSTRACT

An ophthalmic lens suited for extended-wear periods of at least one day on the eye without a clinically significant amount of corneal swelling and without substantial wearer discomfort. The lens has a balance of oxygen permeability and ion or water permeability, with the ion or water permeability being sufficient to provide good on-eye movement, such that a good tear exchange occurs between the lens and the eye. A preferred lens is a copolymerization product of a oxyperm macromer and an ionoperm monomer. The invention encompasses extended wear contact lenses, which include a core having oxygen transmission and ion transmission pathways extending from the inner surface to the outer surface.

27 Claims, 1 Drawing Sheet

OTHER PUBLICATIONS

Tyler's Quarterly Soft Contact Lens Parameter Guide, Sep. 2000, Professional Edition.

"Silicone Hydrogels for Contact Lens Application", Kunzler, Jay F.

Transparent Multiphasic Oxygen Permeable Hydrogels Based on Siloxanic Statistical Copolymers, Robert, C., et al., Macromolecular Engineering, Plenum Press, New York, 1995, pp. 117–126.

"Role of Bulky Polysiloxanylalkyl Methacrylates in Oxygen–Permeable Hydrogel Materials", Lai, Yu Chin, Bausch & Lomb.

"Hydrogels Based on Hydrophilic Side–Chain Siloxanes", Kunzler, J. & Ozark, R., Journal of Applied Polymer Science, vol. 55, 611–619.

"Novel Polyurethane–Silicone Hydrogels", Lai, Yu Chin, Journal of Applied Polymer Science, vol. 56, 301–310 (1995).

* cited by examiner

LOTRAFILCON B

MOLECULAR FORMULA

POLYMERIC MATERIALS FOR MAKING CONTACT LENSES

This application claims the benefits under 35 U.S.C. §119(e) of U.S. provisional application No. 60/294,512 filed May 30, 2001 and 60/337,763 filed Nov. 8, 2001.

FIELD OF THE INVENTION

This invention relates broadly to lenses and polymeric materials useful in optic and ophthalmic arts. More specifically, this invention relates to a polymer composition useful in the manufacture of contact lenses. Still more specifically, this invention relates to contact lenses useful as extended-wear contact lenses.

BACKGROUND OF THE INVENTION

In recent years, a wide variety of research has been carried out to develop polymeric materials useful for making extended-wear contact lenses which affect minimally corneal health and give wearers maximal comfort. Ideally, extended-wear contact lenses would display high oxygen permeability, high ion permeability, good wettability, adequate on-eye movement, and tear exchange, all of which are required to maintain corneal health and wear comfort.

There have been many attempts to prepare different polymers having different properties to make extended-wear lenses having some of the above-mentioned desired properties. For example, see U.S. Pat. Nos. 3,808,178; 4,136,250; and 5,070,169 and especially PCT publication WO9631792. In WO9631792, Nicolson et al. teaches a process and polymer composition for making extended-wear lenses having an oxygen transmissibility of at least 70 barrers/mm; an ion permeability characterized either by (1) an Ionoton Ion Permeability Coefficient of greater than about $0.2 \times 10^{-6}$ cm$^2$/sec or (2) an Ionoflux Diffusion Coefficient of greater than about $1.5 \times 10^{-6}$ cm$^2$/min. Extensive research is still carried out with the aim of developing new materials that are suitable for making extended-wear lenses that have minimal adverse effects on corneal health and wearer comfort.

An objective of the invention is to provide a composition that can make an ophthalmic lens having high water content, high ion permeability, an oxygen transmissibility of at least 57 barrers/mm, all of which are sufficient for corneal health and wearer comfort during extended periods of continuous wear.

Another objective of the invention is to provide an ophthalmic lens the surface of which is modified to increase wettability and thereby to increase further the wearer's comfort.

A further objective of the invention is to provide an ophthalmic lens capable of extended continuous wear periods of at least 24 hours without substantial adverse impact on ocular health or consumer comfort, and more preferably, to provide a lens capable of continuous wear of 7 days or more without substantial adverse impact on ocular health or consumer comfort.

Yet another objective of the invention is to provide methods of forming an extended-wear ophthalmic lens.

SUMMARY OF THE INVENTION

The present invention is largely based on the discovery that a polymer composition, that is obtained by modifying the formulation of the polymer composition disclosed by Nicolson et al. (U.S. Pat. No. 5,849,811, herein incorporated by reference in its entirety), can be used to make extended-wear ophthalmic lenses. The lenses disclosed herein have a higher water content, higher ion permeability, and more adequate on-eye movement than those disclosed by Nicolson et al., while they still display an oxygen transmissibility of 57 barrers/mm or higher and are surface treated to optimize ocular compatibility.

It also has been discovered that unlike polymeric materials disclosed by Nicolson et al., the ion and/or water permeability of polymeric materials (or lenses) is not clinically effected by the presence of oxygen in polymerization reactions. Therefore, inert environments can be avoided in the manufacture of lenses. Therefore, lower cost for the production of lenses can be achieved by using a polymer composition of the present invention.

Such results are unexpected, because the polymer composition of the invention comprises a higher content of hydrophilic monomers which would be expected to decrease substantially the oxygen transmissibility of lenses.

The polymer composition of the invention comprises a macromer, a hydrophobic siloxane-containing monomer, and a hydrophilic monomer. The polymer composition of the invention is useful for making ophthalmic lenses which are suited to extended periods of wear in continuous, intimate contact with ocular tissue and tear fluid. The lens displays a balance of oxygen permeability and ion permeability sufficient to maintain good corneal health, adequate movement of the lens on the eye and wearer comfort during extended wear periods. The lens is formed by polymerization, preferably copolymerization. Preferably, the lens includes a core polymeric material and ophthalmically compatible surfaces. In a preferred embodiment, the surface is more hydrophilic and less lipophobic than the core polymeric material.

Another embodiment of the invention is a method of forming an ophthalmic lens having high oxygen permeability and high ion permeability. The method includes the step of forming a core material, having an inner surface and an outer surface, such that at least one pathway for ion transport and at least one pathway for oxygen transport are present from the inner to the outer surface. In a preferred embodiment, the method includes treating the surface of the lens to render the surface more hydrophilic than the core.

A further embodiment of the invention is an ophthalmic lens comprising a polymeric material which has a high oxygen permeability and a high ion or water permeability, the polymeric material being formed from the polymer composition of the invention. The lens displays a balance of oxygen permeability, ion permeability, water content and favorable modulus of elasticity, all of which sufficient to maintain good corneal health, adequate movement of the lens on the eye and wearer comfort during extended wear periods.

Yet another embodiment of the invention is a method of using a contact lens of the invention as an extended wear lens. The method includes (a) applying the lens to the ocular environment and (b) allowing the lens to remain in intimate contact with the ocular environment for a period of at least 24 hours without substantial adverse impact on corneal health or wearer comfort. A preferred method includes additional steps of (c) removing the lens from the ocular environment; (d) disinfecting the lens; (e) applying the lens to the ocular environment; and (f) allowing the lens to remain in intimate contact with the ocular environment for a period of at least an additional 24 hours. In a preferred embodiment, the lens is worn for a continuous period of at least 4 days without substantial adverse impact on corneal health or wearer comfort.

DESCRIPTION OF THE PREFERRED EMBODIMENTS

Figure 1:
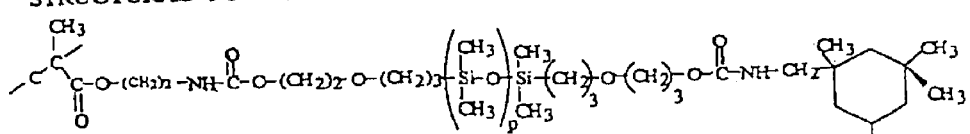
FIG. 1 shows the structure of a preferred macromer.
Figure 1:
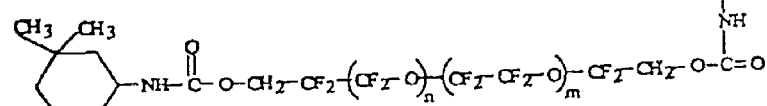
Figure 1:
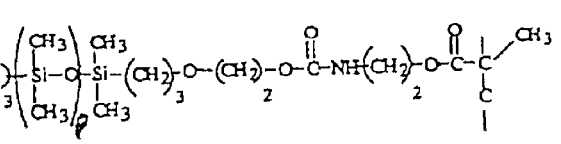
Figure 1:
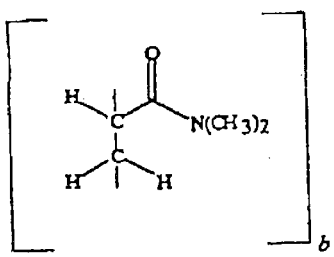
Figure 1:
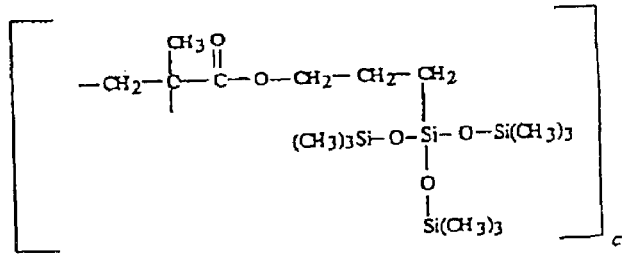

In one aspect, the present invention provides an ophthalmically compatible, transparent lens suited to extended periods of continuous contact with ocular tissue and tear fluids. A particularly preferred embodiment of the invention is an extended-wear vision correction lens suited for safe and comfortable long term wear without removal.

In a preferred embodiment, an ophthalmic lens of the present invention, suited to extended periods of wear in continuous, intimate contact with ocular tissue and ocular fluids, comprises ophthalmically compatible inner and outer surfaces, wherein said ophthalmic lens has an oxygen transmissibility of at least about 57 barrers/mm and an ion permeability characterized by an ionoflux diffusion coefficient of greater than $6.4 \times 10^4$ mm$^2$/min, wherein said ophthalmic lens is formed from a polymer composition comprising: a polymerizable macromer, a siloxane-containing monomer, and a hydrophilic monomer. In a further preferred embodiment, the ophthalmic lens of the present invention further has a water content of greater than 28%, based on total polymer weight.

The "outer surface" of a lens, as used herein, refers to the surface of the lens which faces away from the eye during wear. The outer surface, which is typically substantially convex, may also be referred to as the front curve of the lens. The "inner surface" of a lens, as used herein, refers to the surface of the lens which faces towards the eye during wear. The inner surface, which is typically substantially concave, may also be referred to as the base curve of the lens.

"Ophthalmically compatible", as used herein, refers to a material or surface of a material which may be in intimate contact with the ocular environment for an extended period of time without significantly damaging the ocular environment and without significant user discomfort. Thus, an ophthalmically compatible contact lens will not produce significant corneal swelling, will adequately move on the eye with blinking to promote adequate tear exchange, will not have substantial amounts of lipid adsorption, and will not cause substantial wearer discomfort during the prescribed period of wear.

"Ocular environment", as used herein, refers to ocular fluids (e.g., tear fluid) and ocular tissue (e.g., the cornea) which may come into intimate contact with a contact lens used for vision correction, drug delivery, wound healing, eye color modification, or other ophthalmic applications.

The "oxygen transmissibility" of a lens, as used herein, is the rate at which oxygen will pass through a specific ophthalmic lens. Oxygen transmissibility, Dk/t, is conventionally expressed in units of barrers/mm, where t is the average thickness of the material [in units of mm] over the area being measured and "barrer/mm" is defined as:

[(cm$^3$ oxygen)/(cm$^2$)(sec)(mm$^2$ Hg)]$\times 10^{-9}$

The "oxygen permeability", Dk, of a lens material does not depend on lens thickness. Oxygen permeability is the rate at which oxygen will pass through a material. Oxygen permeability is conventionally expressed in units of barrers, where "barrer" is defined as:

[(cm$^3$ oxygen)(mm)/(cm$^2$)(sec)(mm$^2$ Hg)]$\times 10^{-10}$

These are the units commonly used in the art. Thus, in order to be consistent with the use in the art, the unit "barrer" will have the meanings as defined above. For example, a lens having a Dk of 90 barrers ("oxygen permeability barrers") and a thickness of 90 microns (0.090 mm) would have a Dk/t of 100 barrers/mm (oxygen transmissibility barrers/mm).

The cornea receives oxygen primarily from the corneal surface which is exposed to the environment, in contrast to other tissues which receives oxygen from blood flow. Thus, an ophthalmic lens which may be worn on the eye for extended periods of time must allow sufficient oxygen to permeate through the lens to the cornea to sustain corneal health. One result of the cornea receiving an inadequate amount of oxygen is that the cornea will swell. Therefore, the oxygen transmissibility of an extended-wear lens from the outer surface to the inner surface must be sufficient to prevent any substantial corneal swelling during the period of extended wear. It is known that the cornea swells approximately 3% to 4% during overnight periods of sleep when the eyelids are closed, as a result of oxygen deprivation. It is also known that wearing a typical contact lens, such as ACUVUE (Johnson & Johnson), for a period of about 8 hours (overnight wear) causes corneal swelling of about 11%. However, a preferred extended-wear contact lens will produce, after wear of about 24 hours, including normal sleep periods, corneal swelling of less than about 8%, more preferably less than about 6%, and most preferably less than about 4%. A preferred extended-wear contact lens will produce, after wear of about 7 days, including normal sleep periods, corneal swelling of less than about 10%, more preferably less than about 7%, and most preferably less than about 5%.

The oxygen permeability of a lens and oxygen transmissibility of a lens material may be determined by the method disclosed by Nicolson et al. (U.S. Pat. No. 5,849,811).

It is known that on-eye movement of the lens is required to ensure good tear exchange, and ultimately, to ensure good corneal health. Ion permeability is one of the predictors of on-eye movement, because the permeability of ions is believed to be directly proportional to the permeability of water.

It has been theorized by Nicolson et al. that water permeability is an exceptionally important feature for an extended-wear lens which includes oxyperm polymers such as those disclosed herein. Siloxane-containing materials having high oxygen permeability and low water permeability tend to adhere strongly to the eye, thereby stopping on-eye movement. The ability to pass water through the lens is believed to allow a siloxane-containing polymeric lens to move on the eye, where the movement occurs via forces exerted by water being sqeezed out of the lens. The water permeability of the lens is also believed important in replenishing lens water content once pressure is removed.

Nicolson et al. also found that above a certain threshhold of ion permeability through a lens, from the inner surface of the lens to the outer, or vice versa, the lens will move on the eye, and below the threshhold the lens will adhere to the eye.

The ion permeability through a lens correlates with both the Ionoflux Diffusion Coefficient and the Ionoton Ion Permeability Coefficient.

The Ionoflux Diffusion Coefficient, D, is determined by applying Fick's law as follows:

$D = -n'/(A \times dc/dx)$ where n'=rate of ion transport [mol/min]
A=area of lens exposed [mm$^2$]
D=Ionoflux Diffusion Coefficient[mm$^2$/min]
dc=concentration difference [mol/L]
dx=thickness of lens [mm]

The Ionoton Ion Permeability Coefficient, P, is then determined in accordance with the following equation:

$$\ln(1-2C(t)/C(0)) = -2APt/Vd$$

where:
C(t)=concentration of sodium ions at time t in the receiving cell
C(0)=initial concentration of sodium ions in donor cell
A=membrane area, i.e., lens area exposed to cells
V=volume of cell compartment (3.0 ml)
d=average lens thickness in the area exposed
P=permeability coefficient An Ionoflux Diffusion Coefficient, D, of greater than about $0.2 \times 10^{-3}$ mm$^2$/min is preferred, while greater than about $0.64 \times 10^{-3}$ mm$^2$/min is more preferred and greater than about $1.0 \times 10^{-3}$ mm$^2$/ is most preferred.

The water permeability of a lens may be determined by the Hydrodell Technique described by Nicolson et al. in U.S. Pat. No. 5,849,811. This technique may be used to determine the likelihood of adequate on-eye movement.

The ophthalmic lenses of one embodiment of the present invention have a Hydrodell Water Permeability Coefficient of greater than about $0.2 \times 10^{-6}$ cm$^2$/min. The ophthalmic lenses in a preferred embodiment of the invention have Hydrodell Water Permeability Coefficient of greater than about $0.3 \times 10^{-6}$ cm$^2$/min. The ophthalmic lenses in a preferred embodiment of the invention have Hydrodell Water Permeability Coefficient of greater than about $0.4 \times 10^{-6}$ cm$^2$/min.

On-eye movement of a lens may be also predicted from the mechanical properties of a lens, the ion or water permeability through the lens, or both the mechanical properties and ion or water permeability. In fact, on-eye movement may be predicted more accurately from a combination of mechanical properties and ion or water permeability.

It has been determined that the tensile modulus (modulus of elasticity, E) and the short relaxation time constant ($t_1$) correlate well with on-eye movement. In order to have appropriate on-eye movement, a lens preferably has a tensile modulus of less than about 1.5 MPa. More preferably, E is less than about 1.0 MPa while a particularly preferred E is about 0.5 to about 1.0 MPa.

A preferred short relaxation time constant ($t_1$) is greater than about 3.5 seconds. More preferably, $t_1$ is greater than about 4 seconds, while a particularly preferred $t_1$ is greater than about 4.5 seconds.

Tensile modulus and relaxation time constant ($t_1$) may be measured according to the methods disclosed by Nicolson et al. (U.S. Pat. No. 5,849,811).

In order to assure appropriate on-eye movement of a lens, one may select materials which have a combination of the above-discussed properties. Therefore, a preferred group of extended-wear contact lens materials have (a) a modulus of elasticity (E) of about 1.0 MPa or less, (b) a short relaxation time constant ($t_1$) of greater than about 4 seconds, and (c) an Ionoton Ion Permeability Coefficient of greater than about $0.3 \times 10^{-6}$ cm$^2$/sec and/or an Ionoflux Diffusion Coefficient greater than about $6.4 \times 10^{-4}$ mm$^2$/min.

The water content of a lens can be measured according to Bulk Technique as disclosed in U.S. Pat. No. 5,849,811. Preferably, the lens has a water content of about 28 to 38 weight percent, based on the total lens weight.

The ophthalmic lens of the invention is made from a polymer composition which comprises a macromer, a hydrophobic siloxane-containing monomer, and a hydrophilic monomer A "macromer", as used herein, refers to a polymerizable material which has a molecular weight of at least about 800 grams/mol. The term "macromer", as used herein, also encompasses oligomers.

The macromer is selected from the group consisting of Macromer A, Macromer B, Macromer C, and Macromer D.

Macromer A

Macromer A is a polysiloxane macromer having the the segment of the formula:

CP-PAO-DU-ALK-PDMS-ALK-DU-PAO-CP where PDMS is a divalent poly(disubstituted siloxane), ALK is an alkylene or alkylenoxy group having at least 3 carbon atoms, DU is a diurethane-containing group, PAO is a divalent polyoxyalkylene, and CP is selected from acrylates and methacrylates, wherein said macromer has a number-average molecular weight of 2000 to 10,000.

A preferred polysiloxane macromer segment is defined by the formula

CP-PAO-DU-ALK-PDMS-ALK-DU-PAO-CP where PDMS is a divalent poly(disubstituted siloxane); CP is an isocyanatoalkyl acrylate or methacylate, preferably isocyanatoethyl methacrylate, where the urethane group is bonded to the terminal carbon on the PAO group; PAO is a divalent polyoxyalkylene (which may be substituted), and is preferably a polyethylene oxide, i.e., (—CH$_2$CH$_2$—O—)$_m$CH$_2$CH$_2$— where m may range from about 3 to about 44, more preferably about 4 to about 24; DU is a diurethane, preferably including a cyclic structure, where an oxygen of the urethane linkage (1) is bonded to the PAO group and an oxygen of the urethane linkage (2) is bonded to the ALK group; and ALK is an alkylene or alkylenoxy group having at least 3 carbon atoms, preferably a branched alkylene group or an alkylenoxy group having 3 to 6 carbon atoms, and most preferably a sec-butyl (i.e., —CH$_2$CH$_2$CH(CH$_3$)—) group or an ethoxypropoxy group (e.g., —O—(CH$_2$)$_2$—O—(CH$_2$)$_3$—).

It will be noted that the DU group can be formed from a wide variety of diisocyanates or triisocyanates, including aliphatic, cycloaliphatic or aromatic polyisocyanates. These isocyanates include, without limitation thereto, ethylene diisocyanate; 1,2-diisocyanatopropane; 1,3-diisocyanatopropane; 1,6-diisocyanatohexane; 1,2-diisocyanatocyclohexane; 1,3-diisocyanatocyclohexane; 1,4-diisocyanatobenzene, bis(4-isocyanatocyclohexyl)methane; bis(4-isocyanatocyclohexyl)methane; bis(4-isocyanatophenyl)methane; 1,2- and 1,4-toluene diisocyanate; 3,3-dichloro-4,4'-diisocyanatobiphenyl; tris(4-isocyanatophenyl)methane; 1,5-diisocyanatonaphthalene; hydrogenated toluene diisocyanate; 1-isocyanatomethyl-5-isocyanato-1,3,3-trimethylcyclohexane (i.e., isophorone diisocyanate); 1,3,5-tris(6-isocyanatohexyl)biuret; 1,6-diisocyanato-2,2,4-(2,4,4)-trimethylhexane; 2,2'-diisocyanatodiethyl fumarate; 1,5-diisocyanato-1-carboxypentane; 1,2-, 1,3-, 1,6-, 1,7-, 1,8-, 2,7- and 2,3-diisocyanatonaphthal 2,4- and 2,7-diisocyanato-1-methylnaphthalene; 1,4-diisocyanatomethylcyclohexane; 1,3-diisocyanato-6(7)-methylnaphthalene; 4,4'-diisocyanatobiphenyl; 4,4'-diisocyanato-3,3'-dimethoxybisphenyl; 3,3'- and 4,4'-diisocyanato-2,2'-dimethylbisphenyl; bis(4-isocyanatophenyl)ethane; bis(4-isocyanatophenyl ether); 1,2- or 1,4-toluene diisocyanate; and mixtures thereof. Preferably DU is formed from isophorone diisocyanate or toluene diisocyanate, and more preferably, isophorone diisocyanate, where one isomeric diurethane structure of isophorone diisocyanate is defined above.

A preferred polysiloxane macromer segment has the following formula:

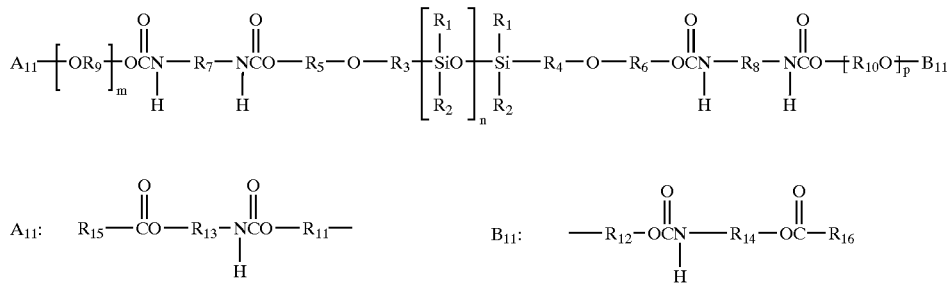

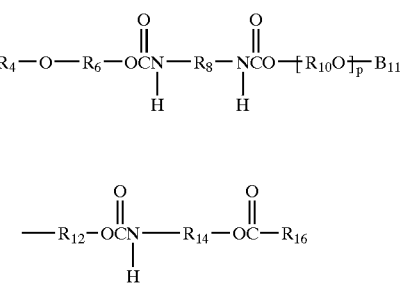

wherein: $R_1$ and $R_2$ are selected from $C_1$–$C_6$ alkyl; $R_3$, $R_4$, $R_5$, and $R_6$ are selected from $C_1$–$C_6$ alkylene; $R_7$ and $R_8$ are selected from linear or branched alkylene and bivalent cycloalkylene; $R_9$, $R_{10}$, $R_{11}$, and $R_{12}$ are selected from $C_1$–$C_2$ alkylene; $R_{13}$ and $R_{14}$ are selected from $C_1$–$C_6$ alkylene; $R_{15}$ and $R_{16}$ are selected from linear or branched lower alkenylene; m and p, independently of one another, are about 3 to about 44; and n is about 13 to about 80, wherein said macromer has a number-average molecular weight of 2000 to 10,000.

The polysiloxane macromer may be synthesized by the following preferred process. At about room temperature (about 20°–25° C.), poly(dimethylsiloxane)dialkanol having hydroxyalkyl (e.g., hydroxy-sec-butyl) or hydroxyalkoxy (e.g., hydroxyethylpropoxy) end groups and having a molecular weight of about 2000 to 3000 preferably about 2200, i.e., having about 28 repeating siloxane groups) is reacted with isophorone diisocyanate at about a 1:2 molar ratio, using about 0.2 weight percent (based on polydimethylsiloxane)dibutyltin dilaurate added as a catalyst The reaction is carried out for about 36 to 60 hours. To this mixture is added poly(ethylene glycol) having a molecular weight of about 400 to 1200 (more preferably about 500 to 700) at about a 2:1 or 2.1:1 molar ratio with respect to the PDMS, about 0.4 to 0.5 weight percent dibutyltin dilaurate (based on polyethylene glycol weight), and chloroform sufficient to ensure substantial mixture homogeneity. The mixture is agitated for about 12 to 18 hours, then held at a temperature of about 44.degree. to 48.degree. C. for about 6 to 10 hours. Excess chloroform is evaporated therefrom at about room temperature to produce a composition having about 50 weight percent solids. Then, isocyanatoethyl methacrylate is added to the mixture in about a 2:1 to 2.3:1 molar ratio with respect to PDMS. The mixture is agitated at room temperature for about 15 to 20 hours. The resulting solution contains a polysiloxane macromer having the composition described above and a number-average molecular weight of about 2000 to 10,000, more preferably about 3000 to 5000.

Macromer B

Macromer B is a polysiloxane-comprising perfluoroalkyl ether and has the formula:

$$P_1\text{-}(Y)_m\text{-}(L\text{-}X_1)p\text{-}Q\text{-}(X_1\text{-}L)_p\text{-}(Y)_m\text{-}P_1$$

where each $P_1$, independently of the others, is a free-radical-polymerizable group;

each Y, independently of the others, is —CONHCOO—, —CONHCONH—, —OCONHCO—, —NHCONHCO—, —NHCO—, —CONH—, —NHCONH—, —COO—, —OCO—, —NHCOO— or —OCONH—;

m and p, independently of one another, are 0 or 1;

each L, independently of the others, is a divalent radical of an organic compound having up to 20 carbon atoms;

each $X_1$, independently of the others, is —NHCO—, —CONH—, —NHCONH—, —COO—, —OCO—, —NHCOO— or —OCONH—; and Q is a bivalent polymer fragment consisting of the segments:

$$\text{-}(E)_k\text{-Z-}CF_2\text{—}(OCF_2)_x\text{—}(OCF_2CF_2)_y\text{—}OCF_2\text{-Z-}(E)_{k'}\text{-},\quad (a)$$

where x+y is a number in the range of from 10 to 30;

each Z, independently of the others, is a divalent radical having up to 12 carbon atoms or Z is a bond;

each E, independently of the others, is —$(OCH_2CH_2)_q$—, where q has a value of from 0 to 2, and where the link -Z-E- represents the sequence -Z-$(OCH_2CH_2)_q$—; and k is 0 or 1;

(b)

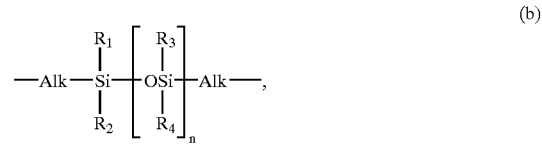

where n is an integer from 5 to 100;

Alk is alkylene having up to 20 carbon atoms;

80–100% of the radicals $R_1$, $R_2$, $R_3$ and $R_4$, independently of one another, are alkyl and 0–20% of the radicals $R_1$, $R_2$, $R_3$ and $R_4$, independently of one another, are alkenyl, aryl or cyanoalkyl; and $$X_2\text{—}R\text{—}X_2,\quad (c)$$

where R is a divalent organic radical having up to 20 carbon atoms, and each $X_2$, independently of the others, is —NHCO—, —CONH—, —NHCONH—, —COO—, —OCO—, —NHCOO— or OCONH—;

with the provisos that there must be at least one of each segment (a), (b), and (c) in Q, that each segment (a) or (b) has a segment (c) attached to it, and that each segment (c) has a segment (a) or (b) attached to it.

The number of segments (b) in the polymer fragment Q is preferably greater than or equal to the number of segments (a). The ratio between the number of segments (a) and (b) in the polymer fragment Q is preferably 3:4, 2:3, 1:2 or 1:1. The molar ratio between the number of segments (a) and (b) in the polymer fragment Q is more preferably 2:3, 1:2 or 1:1.

The mean molecular weight of the polymer fragment Q is in the range of about 1000 to about 20000, preferably in the range of about 3000 to about 15000, particularly preferably in the range of about 5000 to about 12000.

The total number of segments (a) and (b) in the polymer fragment Q is preferably in the range of 2 to about 11, particularly preferably in the range of 2 to about 9, and in particular in the range of 2 to about 7. The smallest polymer unit Q is preferably composed of one perfluoro segment (a), one siloxane segment (b) and one segment (c).

In a preferred embodiment of the polymer fragment Q, which preferably has a composition in the above-mentioned ratios, the polymer fragment Q is terminated at each end by a siloxane segment (b).

The compositions in a bivalent polymer fragment Q always correspond above and below to a mean statistical composition. This means that, for example, even individual block copolymer radicals containing identical recurring units are included, so long as the final mean statistical composition is as specified.

$X_1$ is preferably —NHCONH—, —NHCOO— or —OCONH—, particularly preferably —NHCOO— or —OCONH—.

The $X_2$—R—$X_2$ segment is preferably a radical derived from a diisocyanate, where each $X_2$, independently of the other, is NHCONH—, —NHCOO— or —OCONH—, in particular —NHCOO— or —OCONH—.

Z is preferably a bond, lower alkylene or —CONH-arylene, in which the —CO— moiety is linked to a $CF_2$ group. Z is particularly preferably lower alkylene, in particular methylene.

q is preferably 0, 1, 1.5 or 2, particularly preferably 0 or 1.5.

The perfluoroalkoxy units $OCF_2$ and $OCF_2$ $CF_2$ with the indices x and y in segment (a) can either have a random distribution or be in the form of blocks in a chain. The sum of the indices x+y is preferably a number in the range of 10 to 25, particularly preferably of 10 to 15. The ratio x:y is preferably in the range of 0.5 to 5, in particular in the range of 0.7 to 1.1.

A free-radical-polymerizable group $P_1$ is, for example, alkenyl alkenylaryl or alkenylarylenealkyl having up to 20 carbon atoms. Examples of alkenyl are vinyl, allyl, 1-propen-2-yl, 1-buten-2-, -3- and 4-yl, 2-buten-3-yl, and the isomers of pentenyl, hexenyl, octenyl, decenyl and undecenyl. Examples of alkenylaryl are vinylphenyl, vinylnaphthyl or allylphenyl. An example of alkenylarylenealkyl is o-, m-, or p-vinylbenzyl.

$P_1$ is preferably alkenyl or alkenylaryl having up to 12 carbon atoms, particularly preferably alkenyl having up to 8 carbon atoms, in particular alkenyl having up to 4 carbon atoms.

Y is preferably —COO—, —OCO—, —NHCONH—, —NHCOO—, —OCONH—, NHCO—or —CONH—, particularly preferably —COO—, —OCO—, NHCO— or —CONH—, and in particular, —COO— or —OCO—.

In a preferred embodiment, the indices, m and p, are not simultaneously zero. If p is zero, m is preferably 1.

L is preferably alkylene, arylene, a saturated bivalent cycloaliphatic group having 6 to 20 carbon atoms, arylenealkylene, alkylenearylene, alkylenearylenealkylene or arylenealkylenearylene.

Preferably, L is a divalent radical having up to 12 carbon atoms, particularly preferably a divalent radical having up to 8 carbon atoms. In a preferred embodiment, L is furthermore alkylene or arylene having up to 12 carbon atoms. A particularly preferred embodiment of L is lower alkylene, in particular lower alkylene having up to 4 carbon atoms.

The divalent radical R is, for example, alkylene, arylene, alkylenearylene, arylenealkylene or arylenealkylenearylene having up to 20 carbon atoms, a saturated bivalent cycloaliphatic group having 6 to 20 carbon atoms or cycloalkylenealkylenecycloalkylene having 7 to 20 carbon atoms.

In a preferred embodiment, R is alkylene, arylene, alkylenearylene, arylenealkylene or arylenealkylenearylene having up to 14 carbon atoms or a saturated divalent cycloaliphatic group having 6 to 14 carbon atoms. In a particularly preferred embodiment, R is alkylene or arylene having up to 12 carbon atoms or a saturated bivalent cycloaliphatic group having 6 to 14 carbon atoms.

In a preferred embodiment, R is alkylene or arylene having up to 10 carbon atoms or a saturated bivalent cycloaliphatic group having 6 to 10 carbon atoms.

In a particularly preferred meaning, R is a radical derived from a diisocyanate, for example from hexane 1,6diisocyanate, 2,2,4-trimethylhexane 1,6-diisocyanate, tetramethylene diisocyanate, phenylene 1,4diisocyanate, toluene 2,4-diisocyanate, toluene 2,6diisocyanate, m- or p-tetramethylxylene diisocyanate, isophorone diisocyanate or cyclohexane 1,4-diisocyanate.

In a preferred meaning, n is an integer from 5 to 70, particularly preferably 10 to 50, in particular 14 to 28.

In a preferred meaning, 80–100%, preferably 85–100%, in particular 90–100%, of the radicals $R_1$, $R_2$, $R_3$ and $R_4$ are, independently of one another, lower alkyl having up to 8 carbon atoms, particularly preferably lower alkyl having up to 4 carbon atoms, especially lower alkyl having up to 2 carbon atoms. A further particularly preferred embodiment of $R_1$, $R_2$, $R_3$ and $R_4$ is methyl.

In a preferred meaning, 0–20%, preferably 0–15%, in particular 0–10%, of the radicals $R_1$, $R_2$, $R_3$ and $R_4$ are, independently of one another, lower alkenyl, unsubstituted or lower alkyl- or lower alkoxy-substituted phenyl or cyano (lower alkyl).

Arylene is preferably phenylene or naphthylene, which is unsubstituted or substituted by lower alkyl or lower alkoxy, in particular 1,3-phenylene, 1,4-phenylene or methyl-1,4-phenylene, 1,5-naphthylene or 1,8-naphthylene.

Aryl is a carbocyclic aromatic radical which is unsubstituted or substituted preferably by lower alkyl or lower alkoxy. Examples are phenyl, tolyl, xylyl, methoxyphenyl, t-butoxyphenyl, naphthyl and phenanthryl.

A saturated bivalent cycloaliphatic group is preferably cycloalkylene, for example cyclohexylene or cyclohexylene (lower alkylene), for example cyclohexylenemethylene, which is unsubstituted or substituted by one or more lower alkyl groups, for example methyl groups, for example trimethylcyclohexylenemethylene, for example the bivalent isophorone radical.

For the purposes of the present invention, the term "lower" in connection with radicals and compounds, unless defined otherwise, denotes, in particular, radicals or compounds having up to 8 carbon atoms, preferably having up to 4 carbon atoms.

Lower alkyl has, in particular, up to 8 carbon atoms, preferably up to 4 carbon atoms, and is, for example, methyl, ethyl, propyl, butyl, tert-butyl, pentyl, hexyl or isohexyl.

Alkylene has up to 12 carbon atoms and can be straight-chain or branched. Suitable examples are decylene, octylene, hexylene, pentylene, butylene, propylene, ethylene, methylene, 2-propylene, 2-butylene, 3-pentylene, and the like.

Lower alkylene is alkylene having up to 8 carbon atoms, particularly preferably up to 4 carbon atoms. Particularly preferred meanings of lower alkylene are propylene, ethylene and methylene.

The arylene unit in alkylenearylene or arylenealkylene is preferably phenylene, unsubstituted or substituted by lower alkyl or lower alkoxy, and the alkylene unit therein is preferably lower alkylene, such as methylene or ethylene, in particular methylene. These radicals are therefore preferably phenylenemethylene or methylenephenylene.

Lower alkoxy has, in particular, up to 8 carbon atoms, preferably up to 4 carbon atoms, and is, for example, methoxy, ethoxy, propoxy, butoxy, tert-butoxy or hexyloxy.

Arylenealkylenearylene is preferably phenylene(lower alkylene)phenylene having up to 8, in particular up to 4, carbon atoms in the alkylene unit, for example phenyleneethylenephenylene or phenylenemethylenephenylene.

Macromer B can be prepared by known processes, for example as described in U.S. Pat. No. 5,849,811, herein incorporated by reference.

Macromer C

Macromer C are a class of macromers which contain free hydroxyl groups. This class of macromers are built up, for example, from an amino-alkylated polysiloxane which is derivatized with at least one polyol component containing an unsaturated polymerizable side chain. Polymers can be prepared on the one hand from this class of macromers according to the invention by homopolymerization. The macromers mentioned furthermore can be mixed and polymerized with one or more hydrophilic and/or hydrophobic comonomers. A special property of the macromers according to the invention is that they function as the element which controls microphase separation between selected hydrophilic and hydrophobic components in a crosslinked end product. The hydrophilic/hydrophobic microphase separation is in the region of less than 300 nm. The macromers are preferably crosslinked at the phase boundaries between, for example, an acrylate comonomer on the one hand and an unsaturated polymerizable side chain of polyols bonded to polysiloxane on the other hand, by covalent bonds and additionally by reversible physical interactions, for example hydrogen bridges. These are formed, for example, by numerous amide or urethane groups. The continuous siloxane phase which exists in the phase composite has the effect of producing a surprisingly high permeability to oxygen.

In an embodiment, macromer c comprises at least one segment of the formula (I):

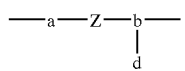  (I)

in which (a) is a polysiloxane segment, (b) is a polyol segment which contains at least 4 C atoms, Z is a segment (c) or a group $X_1$, (c) is defined as $X_2$—R—$X_2$, wherein R is a bivalent radical of an organic compound having up to 20 C atoms and each $X_2$ independently of the other is a bivalent radical which contains at least one carbonyl group, $X_1$ is defined as $X_2$, and (d) is a radical of the formula (II):

$$X_3\text{-}L\text{-}(Y)_k\text{-}P_1 \quad (II)$$

in which $P_1$ is a group which can be polymerized by free radicals; Y and $X_3$ independently of one another are a bivalent radical which contains at least one carbonyl group; k is 0 or 1; and L is a bond or a divalent radical having up to 20 C atoms of an organic compound.

A polysiloxane segment (a) is derived from a compound of the formula (III):

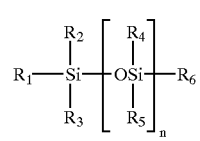  (III)

in which n is an integer from 5 to 500; 99.8–25% of the radicals $R_1$, $R_2$, $R_3$, $R_4$, $R_5$ and $R_6$ independently of one another are alkyl and 0.2–75% of the radicals $R_1$, $R_2$, $R_3$, $R_4$, $R_5$ and $R_6$ independently of one another are partly fluorinated alkyl, aminoalkyl, alkenyl, aryl, cyanoalkyl, alk-NH-alk-$NH_2$ or alk-$(OCH_2)_m$—$(OCH_2)$p-$OR_7$, $R_7$ is hydrogen or lower alkyl, alk is alkylene, and m and p independently of one another are an integer from 0 to 10, one molecule containing at least one primary amino or hydroxyl group.

The alkylenoxy groups —$(OCH_2CH_2)_m$ and —$(OCH_2)_p$ in the siloxane of the formula (III) are either distributed randomly in a ligand alk-$(OCH_2CH_2)_m$—$(OCH_2)_p$—$OR_7$ or are distributed as blocks in a chain.

A polysiloxane segment (a) is linked a total of 1–50 times, preferably 2–30 times, and in particular 4–10 times, via a group Z with a segment (b) or another segment (a), Z in an a-Z-a sequence always being a segment (c). The linkage site in a segment (a) with a group Z is an amino or hydroxyl group reduced by one hydrogen.

In a preferred embodiment, a polysiloxane segment is derived from a compound of the formula (III) in which the radicals $R_1$, $R_2$, $R_3$, $R_4$, $R_5$ and $R_6$ are a total of 1–50 times, preferably 2–30 times, and in particular 4–10 times, independently either terminally or pendently aminoalkyl or hydroxyalkyl, the other variables being as defined above.

In a preferred embodiment, a polysiloxane segment is derived from a compound of the formula (III) in which 95–29% of the radicals $R_1$, $R_2$, $R_3$, $R_4$, $R_5$ and $R_6$ independently of another are alkyl and 5–71% of the radicals $R_1$, $R_2$, $R_3$, $R_4$, $R_5$ and $R_6$ independently of on another are partly fluorinated alkyl, aminoalkyl, alkenyl, aryl, cyanoalkyl, alk-NH-alk-$NH_2$ or alk-$(OCH_2CH_2)_m$—$(OCH_2)_p$—$OR_7$, and in which the variables are as defined above.

In a preferred meaning, n is an integer from 5 to 400, more preferably 10 to 250 and particularly preferably 12 to 125.

In a preferred meaning, the two terminal radicals $R_1$ and $R_6$ are aminoalkyl or hydroxyalkyl, the other variables being as defined above.

In another preferred meaning, the radicals $R_4$ and $R_5$ are 1–50 times, more preferably 2–30 times and in particular 4–10 times pendently aminoalkyl or hydroxyalkyl and the other variables are as defined above.

In another preferred meaning, the radicals $R_1$, $R_2$, $R_3$, $R_4$, $R_5$ and $R_6$ are a total of 1–50 times, more preferably 2–30 times and in particular 4–10 times, independently both terminally and pendently aminoalkyl or hydroxyalkyl and the other variables are as defined above.

If Z is $X_1$, $X_1$ is a bivalent group which contains at least one carbonyl group. A carbonyl group mentioned is flanked in any manner, if appropriate, by —O—, —CONH—, —NHCO— or —NH—.

Examples of bivalent groups Z are typically carbonyls, esters, amides, urethanes, ureas or carbonates.

$X_1$ is preferably an ester, amide, urethane or urea group, in particular an ester or amide group.

$X_2$ is defined in the same way as $X_1$ and is preferably an ester, amide, urethane, carbonate or urea group, more preferably an ester, amide, urethane or urea group and in particular an amide, urethane or urea group.

If Z in formula (I) is $X_1$, a polyol segment b is preferably understood as meaning a polyol derived from a carbohydrate, carbohydrate monolactone or carbohydrate dilactone. A carbohydrate is understood as meaning a mono-, di-, tri-, tetra-, oligo- or polysaccharide. A carbohydrate lactone is understood as meaning the lactone of an aldonic or uronic acid. An aldonic or uronic acid is, for example, a carboxylic acid formed by oxidation of a mono-, di-, tri-, tetra-, oligo- or polysaccharide. Examples of aldonic acid lactones are gluconolactone, galactonolactone, lactobionolactone or maltoheptaonolactone; examples of uronic acid lactones are glucuronic acid lactone, mannuronic acid lactone or iduronic acid lactone. An example of a carbohydrate dilactone is D-glucaro-1,4:6,3-dilactone.

A carbohydrate lactone reacts, for example, with a primary amino group or a hydroxyl group of segment (a) to form a covalent amide or ester bond of the type $X_1$. Such linkages are the constituent of a further preferred embodiment of macromers according to the invention. Such macromers have an alternating distribution of segments of type (a) and (b) which are interrupted by $X_1$.

In another embodiment, macromer C is defined by the formula (IV):

(IV)

in which the variables are as defined above.

In another embodiment, macromer C is defined by the formula (V):

(V)

in which the polysiloxane segment (a) contains q pendent ligands; x is 0, 1 or 2; q has an average numerical value of 1–20, preferably 1–10, and in particular 1–5; and the segments (b) in a macromer according to the formula (V) are linked in total (per molecule) with up to 20, preferably with up to 15, and in particular with up to 6 polymerizable segments (d).

In another embodiment, macromer C has the formula (VI):

(VI)

in which a linear sequence is present; x is 0, 1 or 2; q has an average numerical value of 1–20, preferably 1–10, and in particular 1–5; and the segments (b) in a macromer according to the formula (VI) are linked in total (per molecule) with up to 20, preferably with up to 15, and in particular with up to 6 polymerizable segments (d).

In another embodiment, macromer C has the formula (VII):

(VII)

in which x is 0, 1 or 2; and the average number of segments (d) per molecule of the formula (VII) is preferably in the range from 2 to 5, and very preferably is in the range from 3 to 4.

A polyol segment (b) is derived from a polyol which carries no lactone group if the group Z is a segment (c). Examples of such polyols are a 1,2-polyol, for example the reduced monosaccharides, for example mannitol, glucitol, sorbitol or iditol, a 1,3-polyol, for example polyvinyl alcohol (PVA), which is derived from partly or completely hydrolysed polyvinyl acetate, and furthermore amino-terminal PVA telomers, aminopolyols, aminocyclodextrins, aminomono-, -di-, -tri-, -oligo- or -polysaccharides or cyclodextrin derivatives, for example hydroxypropylcyclodextrin. An abovementioned carbohydrate dilactone can be reacted, for example, with preferably 2 equivalents of an amino-terminal PVA telomer to give a polyol macromer which carries, in the central part, the carbohydrate compound derived from the dilactone. Such polyols of this composition are likewise understood to be a suitable polyol.

As illustrated in formula (I), a segment (b) carries at least one vinylic polymerizable segment (d), a linkage of a segment (d) via the bivalent radical $X_3$ thereof to an amino or hydroxyl group, of a segment (b), reduced by a hydrogen atom being intended.

A vinylic polymerizable segment (d) is incorporated either terminally or pendently preferably 1–20 times, more preferably 2–15 times, and in particular 2–6 times, per macromer molecule according to the invention.

A vinylic polymerizable segment (d) is incorporated terminally and also pendently as desired (as a terminal/pendent mixture) preferably 1–20 times, more preferably 2–15 times and in particular 2–6 times, per macromer molecule according to the invention.

A group $P_1$ which can be polymerized by free radicals is, for example, alkenyl, alkenylaryl or alkenylarylenealkyl having up to 20 C atoms. Examples of alkenyl are vinyl, allyl, 1-propen-2-yl, 1-buten-2- or -3- or -4-yl, 2-buten-3-yl and the isomers of pentenyl, hexenyl, octenyl, decenyl or undecenyl. Examples of alkenylaryl are vinylphenyl, vinylnaphthyl or allylphenyl. An example of alkenylarylenealkyl is vinylbenzyl.

$P_1$ is preferably alkenyl or alkenylaryl having up to 12 C atoms, more preferably alkenyl having up to 8C atoms and in particular alkenyl having up to 4 C atoms.

L is preferably alkylene, arylene, a saturated bivalent cycloaliphatic group having 6 to 20 carbon atoms, arylenealkylene, alkylenearylene, alkylenearylenealkylene or arylenealkylenearylene. In a preferred meaning, L furthermore is preferably a bond.

In a preferred meaning, L is a divalent radical having up to 12 C atoms, and more preferably a divalent radical having up to 8 C atoms. In a preferred meaning, L furthermore is alkylene or arylene having up to 12 C atoms. A very preferred meaning of L is lower alkylene, in particular lower alkylene having up to 4C atoms.

Y is preferably a carbonyl, ester, amide or urethane group, in particular a carbonyl, ester or amide group, and very preferably a carbonyl group.

In another preferred meaning, Y is absent, i.e., k is 0.

In a preferred meaning, $X_3$ is a urethane, urea, ester, amide or carbonate group, more preferably a urethane, urea, ester or amide group, and in particular a urethane or urea group.

A vinylic polymerizable segment (d) is derived, for example, from acrylic acid, methacrylic acid, methacryloyl chloride, 2-isocyanatoethyl methacrylate (IEM), allyl isocyanate, vinyl isocyanate, the isomeric vinylbenzyl isocyanates or adducts of hydroxyethyl methacrylate (HEMA) and 2,4-tolylene diisocyanate (TDI) or isophorone diisocyanate (IPDI), in particular the 1:1 adduct.

A preferred embodiment of segment (d) is incorporated either terminally or pendently or as a terminal/pendent mixture 5 times.

The diradical R is, for example, alkylene, arylene, alkylenearylene, arylenealkylene or arylenealkylenearylene having up to 20 carbon atoms, a saturated bivalent cycloaliphatic group having 6 to 20 carbon atoms or cycloalkylenealkylenecycloalkylene having 7 to 20 carbon atoms.

In a preferred meaning, R is alkylene, arylene, alkylenearylene, arylenealkylene or arylenealkylenearylene having up to 14 carbon atoms or a saturated bivalent cycloaliphatic group having 6 to 14 carbon atoms.

In a preferred meaning, R is alkylene, arylene, alkylenearylene or arylenealkylene having up to 14 carbon atoms, or a saturated bivalent cycloaliphatic group having 6 to 14 carbon atoms.

In a preferred meaning, R is alkylene or arylene having up to 12 carbon atoms, or a saturated bivalent cycloaliphatic group having 6 to 14 carbon atoms.

In a preferred meaning, R is alkylene or arylene having up to 10 carbon atoms, or is a saturated bivalent cycloaliphatic group having 6 to 10 carbon atoms.

In a very preferred meaning, a segment (c) is derived from a diisocyanate, for example from hexane 1,6-diisocyanate, 2,2,4-trimethylhexane 1,6-diisocyanate, tetramethylene diisocyanate, phenylene 1,4-diisocyanate, toluene 2,4-diisocyanate, toluene 2,6-diisocyanate, m- or p-tetramethylxylene diisocyanate, isophorone diisocyanate or cyclohexane 1,4-diisocyanate.

A preferred embodiment of segment (c) is furthermore derived from a diisocyanate in which the isocyanate groups have different reactivities. The different reactivity is influenced, in particular, by the spatial requirements and/or electron density in the neighbourhood of an isocyanate group.

The average molecular weight of a macromer according to the invention is preferably in the range from about 300 to about 30,000, very preferably in the range from about 500 to about 20,000, more preferably in the range from about 800 to about 12,000, and particularly preferably in the range from about 1000 to about 10,000.

In a preferred embodiment, macromer C has a segment sequence of the formula (VIII):

$$b\text{-}Z\text{-}a\text{-}\{c\text{-}a\}_r\text{-}(Z\text{-}b)_t \qquad (VIII)$$

in which r is an integer from 1 to 10, preferably from 1 to 7, and in particular from 1 to 3; t is 0 or 1, and preferably 1; a linear (c-a) chain which may or may not be terminated by a segment (b) is present (t=1); and the above preferences apply to the total number of segments (d), which are preferably bonded to a segment (b).

In another preferred embodiment, macromer C has a segment sequence of formula (IX):

$$b\text{-}Z\text{-}a\text{-}\{c\text{-}a\text{-}(Z\text{-}b)_t\}_r \qquad (IX)$$

in which the sequence (c-a)-(Z-b)t hangs pendently r times on the segment (a) and may or may not be terminated by a segment (b); r is an integer from 1 to 10, preferably from 1 to 7, and in particular from 1 to 3; t is 0 or 1, and is preferably 1; Z is a segment (c) or a group $X_1$; and the above preferences apply to the total number of segments (d), which are preferably bonded to a segment (b).

Another preferred embodiment of macromer C has a segment sequence of formula (X):

$$b\text{-}c\text{-}\{a\text{-}c\}_s\text{-}B \qquad (X)$$

in which s is an integer from 1 to 10, preferably from 1 to 7, and in particular from 1 to 3; B is a segment (a) or (b); and the above preferences apply to the number of segments (d), which are bonded to a segment (b).

Another preferred embodiment of macromer C has a segment sequence of the formula (XI):

$$B\text{-}(c\text{-}b)_s\text{-}Z\text{-}a\text{-}(b)_t \qquad (XI)$$

in which the structures are linear; s is an integer from 1 to 10, preferably from 1 to 7, and in particular from 1 to 3; B is a segment (a) or (b); t is 0 or 1, and the above preferences apply to the number of segments (d), which are bonded to a segment (b).

The ratio of the number of segments (a) and (b) in a macromer according to the Material "C" embodiment of the invention is preferably in a range of (a):(b)=3:4, 2:3, 1:2, 1:1, 1:3 or 1:4. The total sum of segments (a) and (b) or, where appropriate, (a) and (b) and (c) is in a range from 2 to 50, preferably 3 to 30, and in particular in the range from 3 to 12.

Alkyl has up to 20 carbon atoms and can be straight-chain or branched. Suitable examples include dodecyl, octyl, hexyl, pentyl, butyl, propyl, ethyl, methyl, 2-propyl, 2-butyl or 3-pentyl.

Arylene is preferably phenylene or naphthylene, which is unsubstituted or substituted by lower alkyl or lower alkoxy, in particular 1,3-phenylene, 1,4-phenylene or methyl-1,4-phenylene; or 1,5-naphthylene or 1,8-naphthylene.

Aryl is a carbocyclic aromatic radical, which is unsubstituted or substituted by preferably lower alkyl or lower alkoxy. Examples are phenyl, toluyl, xylyl, methoxyphenyl, t-butoxyphenyl, naphthyl or phenanthryl.

A saturated bivalent cycloaliphatic group is preferably cycloalkylene, for example cyclohexylene or cyclohexylene-lower alkylene, for example cyclohexylenemethylene, which is unsubstituted or substituted by one or more lower alkyl groups, for example methyl groups, for example trimethylcyclohexylenemethylene, for example the bivalent isophorone radical. The term "lower" in the context of this invention in connection with radicals and compounds, unless defined otherwise, means, in particular, radicals or compounds having up to 8 carbon atoms, preferably having up to 4 carbon atoms.

Lower alkyl has, in particular, up to 8 carbon atoms, preferably up to 4 carbon atoms, and is, for example, methyl, ethyl, propyl, butyl, tert-butyl, pentyl, hexyl or isohexyl.

Alkylene has up to 12 carbon atoms and can be straight-chain or branched. Suitable examples include decylene, octylene, hexylene, pentylene, butylene, propylene, ethylene, methylene, 2-propylene, 2-butylene or 3-pentylene.

Lower alkylene is alkylene having up to 8, and particularly preferably having up to 4 carbon atoms. Particularly preferred examples of lower alkylenes are propylene, ethylene and methylene.

The arylene unit of alkylenearylene or arylenealkylene is preferably phenylene, which is unsubstituted or substituted by lower alkyl or lower alkoxy, and the alkylene unit of this is preferably lower alkylene, such as methylene or ethylene, in particular methylene. Such radicals are therefore preferably phenylenemethylene or methylenephenylene.

Lower alkoxy has, in particular, up to 8 carbon atoms, preferably up to 4 carbon atoms, and is, for example, methoxy, ethoxy, propoxy, butoxy, tert-butoxy or hexyloxy.

Partly fluorinated alkyl is understood as meaning alkyl in which up to 90%, preferably up to 70%, and in particular up to 50%, of the hydrogens are replaced by fluorine.

Arylenealkylenearylene is preferably phenylene-lower alkylene-phenylene having up to 8, and in particular having up to 4 carbon atoms in the alkylene unit, for example phenylenethylenephenylene or phenylenemethylenephenylene.

A monosaccharide in the context of the present invention is understood as meaning an aldopentose, aldohexose, aldotetrose, ketopentose or ketohexose.

Examples of an aldopentose are D-ribose, D-arabinose, D-xylose or D-lyose; examples of an aldohexose are D-allose, D-altrose, D-glucose, D-mannose, D-gulose, D-idose, D-galactose, D-talose, L-fucose or L-rhamnose; examples of a ketopentose are D-ribulose or D-xylulose; examples of a tetrose are D-erythrose or threose; and examples of a ketohexose are D-psicose, D-fructose, D-sorbose or D-tagatose. Examples of a disaccharide are trehalose, maltose, somaltose, cellobiose, gentiobiose, saccharose, lactose, chitobiose, N,N-diacetylchitobiose, palatinose or sucrose. Raffinose, panose or maltotriose may be mentioned as an example of a trisaccharide. Examples of an oligosaccharide are maltotetraose, maltohexaose, chitoheptaose and furthermore cyclic oligosaccharides, such as cyclodextrins.

Cyclodextrins contain 6 to 8 identical units of α-1,4-glucose. Some examples are α-, β- and γ-cyclodextrin, derivatives of such cyclodextrins, for example hydroxypropylcyclodextrins, and branched cyclodextrins.

Macromer C can be prepared by processes known per se, for example, according the the procedures disclosed in U.S. Pat. No. 5,849,811.

Macromer D

Macromer D is a siloxane-containing macromer which is formed from a poly(dialkylsiloxane) dialkoxyalkanol having the following structure:

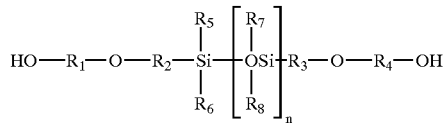

where n is an integer from about 5 to about 500, preferably about 20 to 200, more preferably about 20 to 100;

the radicals $R_1$, $R_2$, $R_3$, and $R_4$, independently of one another, are lower alkylene, preferably $C_1$–$C_6$ alkylene, more preferably $C_1$–$C_3$ alkylene, wherein in a preferred embodiment, the total number of carbon atoms in $R_1$ and $R_2$ or in $R_3$ and $R_4$ is greater than 4; and $R_5$, $R_6$, $R_7$, and $R_8$ are, independently of one another, lower alkyl, preferably $C_1$–$C_6$ alkyl, more preferably $C_1$–$C_3$ alkyl.

The general structure of macromer D is:

ACRYLATE-LINK-ALK-O-ALK-PDAS-ALK-O-ALK-LINK-ACRYLATE where the ACRYLATE is selected from acrylates and methacrylates; LINK is selected from urethanes and dirurethane linkages, ALK-O-ALK is as defined above ($R_1$—O—$R_2$ or $R_3$O—$R_4$), and PDAS is a poly(dialkylsiloxane).

For example, macromer D may be prepared by reacting isophorone diisocyanate, 2-hydroxyethyl (meth)acrylate and a poly(dialkylsiloxane) dialkoxyalkanol in the presence of a catalyst.

A preferred macromer D may be prepared by reacting a slight excess of isocyanatoalkyl methacrylate, especially isocyanatoethyl methacrylate (IEM), with a poly(dialkylsiloxane) dialkoxyalkanol, preferably poly(dimethylsiloxane) dipropoxyethanol, in the presence of a catalyst, especially an organotin catalyst such as dibutyltin dilaurate (DBTL). The primary resulting structure is as follows:

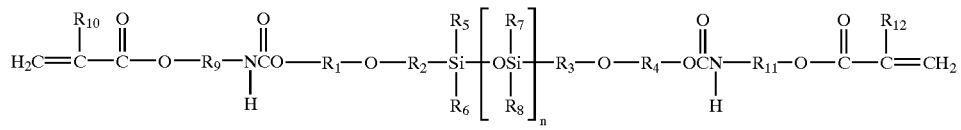

where n is an integer from about 5 to about 500; $R_1$, $R_2$, $R_3$, and $R_4$, independently of one another, are lower alkylene; $R_5$, $R_6$, $R_7$, and $R_8$ are, independently of one another, are alkyl, $R_9$ and $R_{11}$ are alkylene; and $R_{10}$ and $R_{12}$ are methyl or hydrogen.

A preferred polymer composition suitable for making an ophthalmic lens of the invention will include (a) about 20 to 40 weight percent macromer, (b) about 5 to 30 weight percent siloxane-containing monomer, and (c) about 10 to 35 weight percent hydrophilic monomer. More preferably, the siloxane-containing monomer is TRIS. More preferably, the polymer composition of the invention includes a color additive (e.g., copper phthalocyanine) which is capable of creating a light blue edge-to-edge visibility tint. Such tint can facilitate the handling of ophthalmic lenses.

"Molecular weight" of a polymeric material (including monomeric or macromeric materials), as used herein, refers to the number-average molecular weight unless otherwise specifically noted or unless testing conditions indicate otherwise.

A "monomer", as used herein refers to a polymerizable material which has a molecular weight of less than about 800 grams/mol.

"Hydrophilic", as used herein, describes a material or portion thereof which will more readily associate with water than with lipids.

Exemplary siloxane-containing monomers include, without limitation, methacryloxyalkylsiloxanes, tristrimethylsilyloxysilylpropyl methacrylate (TRIS), 3-methacryloxy propylpentamethyldisiloxane and bis(methacryloxypropyl) tetramethyldisiloxane. A preferred siloxane-containing monomer is TRIS, which is referred to 3-methacryloxypropyltris(trimethylsiloxy) silane, and represented by CAS No. 17096-07-0. The term "TRIS" also includes dimers of 3-methacryloxypropyltris (trimethylsiloxy) silane.

A hydrophilic monomer is taken to mean a monomer which typically gives a homopolymer which is soluble in water or can absorb at least 10% by weight of water. Nearly any hydrophilic monomer that can act as a plasticizer can be used in the composition of the invention. Suitable hydrophilic monomers are, without this being an exhaustive list, hydroxyl-substituted lower alkyl ($C_1$ to $C_8$) acrylates and methacrylates, acrylamide, methacrylamide, (lower allyl) acrylamides and -methacrylamides, ethoxylated acrylates and methacrylates, hydroxyl-substituted (lower alkyl)

acrylamides and -methacrylamides, hydroxyl-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl4,4'-dialkyloxazolin-5-one, 2- and 4-vinylpyridine, vinylically unsaturated carboxylic acids having a total of 3 to 5 carbon atoms, amino(lower alkyl)-(where the term "amino" also includes quaternary ammonium), mono(lower alkylamino)(lower alkyl) and di(lower alkylamino)(lower alkyl)acrylates and methacrylates, allyl alcohol and the like.

Among the preferred hydrophilic monomers are N,N-dimethylacrylamide (DMA), 2-hydroxyethylmethacrylate (HEMA), hydroxyethyl acrylate, hydroxypropyl acrylate, hydroxypropyl methacrylate (HPMA), trimethylammonium 2-hydroxy propylmethacrylate hydrochloride, dimethylaminoethyl methacrylate (DMAEMA), dimethylaminoethylmethacrylamide, acrylamide, methacrylamide, allyl alcohol, vinylpyridine, glycerol methacrylate, N-(1,1dimethyl-3-oxobutyl)acrylamide, N-vinyl-2-pyrrolidone (NVP), acrylic acid, methacrylic acid, and N,N-dimethyacrylamide (DMA).

A wide variety of additional polymerizable materials may be included in the polymer composition prior to polymerization. Cross-linking agents, such as ethylene glycol dimethacrylate (EGDMA), may be added to improve structural integrity and mechanical strength. Antimicrobial polymerizable materials such as poly(quaternary ammonium) salts may be added to inhibit microbial growth on the lens material. An especially advantageous polymerizable material is TRIS, which may act both to increase oxygen permeability and to improve the modulus of elasticity.

Ophthalmic lenses of the invention can be made in a manner known per se from the polymer composition by a polymerization reaction in molds for making the ophthalmic lenses with which the expert is familiar. Usually, a mixture of the polymer composition is heated, with the addition of an agent which forms free radicals. Such an agent which forms free radicals is, for example, azoisobutyronitrile (AIBN), potassium peroxodisulfate, dibenzoyl peroxide, hydrogen peroxide or sodium percarbonate. If the compounds mentioned are heated, for example, free radicals are then formed, by homolysis, and can then, for example, initiate a polymerization.

A polymerization reaction can particularly preferably be carried out using a photoinitiator. Photopolymerization is the term used in this case. For photopolymerization, a photoinitiator which can initiate free radical polymerization and/or crosslinking by the use of light is suitably added. Examples of this are familiar to the expert, and specifically, suitable photoinitiators are benzoin methyl ether, 1-hydroxycyclohexyl phenyl ketone and Darocur and Irgacur types, preferably Darocur 1173® and Darocur 2959®. Reactive photoinitiators which can be incorporated, for example, into a macromer or can be used as a special comonomer (a) are also suitable. Examples of these are to be found in EP 632 329. The photopolymerization can then be triggered off by actinic radiation, for example light, in particular UV light of a suitable wavelength. The spectral requirements can be controlled accordingly, if appropriate, by addition of suitable photosensitizers.

Polymerization can be carried out in the presence or absence of a solvent. Suitable solvents are in principle all solvents which dissolve the monomers used, for example water, alcohols, such as lower alkanols, for example ethanol or methanol, and furthermore carboxylic acid amides, such as dimethylformamide, dipolar aprotic solvents, such as dimethyl sulfoxide or methyl ethyl ketone, ketones, for example acteone or cyclohexanone, hydrocarbons, for example toluene, ethers, for example THF, dimethoxyethane or dioxane, and halogenated hydrocarbons, for example trichloroethane, and also mixtures of suitable solvents, for example mixtures of water with an alcohol, for example a water/ethanol or a water/methanol mixture.

If appropriate, a polymer network can be intensified by addition of a so-called crosslinking agent, for example a polyunsaturated monomer, for example, allyl(meth)acrylate, lower alkylene glycol di(meth)acrylate, poly lower alkylene glycol di(meth)acrylate, lower alkylene di(meth)acrylate, divinyl ether, divinyl sulfone, di- or trivinylbenzene, trimethylolpropane tri(meth)acrylate, pentaerythritol tetra(meth)acrylate, bisphenol A di(meth)acrylate, methylenebis(meth)acrylamide, triallyl phthalate or diallyl phthalate.

The amount of a polyunsaturated monomer used is expressed in the weight content with respect to the total polymer and is in the range from 20 to 0.05%, in particular in the range from 10 to 0.1%, and preferably in the range from 2 to 0.1%.

The ophthalmic lenses of the present invention have a surface which is biocompatible with ocular tissue and ocular fluids during the desired extended period of contact. In one preferred embodiment, the ophthalmic lenses of the present invention include a core material, as defined above, surrounded, at least in part, by a surface which is more hydrophilic and lipophobic than the core material. A hydrophilic surface is desirable in order to enhance the compatibility of the lens with the ocular tissues and tear fluids. As surface hydrophilicity increases, undesirable attraction and adherence of lipids and proteinaceous matter typically decreases. There are factors other than surface hydrophilicity, such as immunological response, which may contribute to deposit accumulation on the lens. Deposition of lipids and proteinaceous matter causes haze on the lens, thereby reducing visual clarity. Proteinaceous deposits may also cause other problems, such as irritation to the eye. After extended periods of continuous or intermittent wear, the lens must be removed from the eye for cleaning, i.e., deposit removal. Therefore, increased surface hydrophilicity, and concomittent reductions in deposits of biological matter, allows increased wear time.

"Surface treatment processes", as used herein, refers to processes to render a surface more ophthalmically compatible, in which, by means of contact with a vapor or liquid, and/or by means of application of an energy source (1) a coating is applied to the surface of an article, (2) chemical species are adsorbed onto the surface of an article, (3) the chemical nature (e.g., electrostatic charge) of chemical groups on the surface of an article are altered, or (4) the surface properties of an article are otherwise modified.

There are a variety of methods disclosed in the art for rendering a surface of a material hydrophilic. For example, the lens may be coated with a layer of a hydrophilic polymeric material. Alternatively, hydrophilic groups may be grafted onto the surface of the lens, thereby producing a monolayer of hydrophilic material. These coating or grafting processes may be effected by a number of processes, including without limitation thereto, exposing the lens to plasma gas or immersing the lens in a monomeric solution under appropriate conditions.

Another set of methods of altering the surface properties of a lens involves treatment prior to polymerization to form the lens. For example, the mold may be treated with a plasma (i.e., an ionized gas), a static electrical charge, irradiation, or other energy source, thereby causing the prepolymerzation mixture immediately adjacent the mold surface to differ in composition from the core of the prepolymerization mixture.

A preferred class of surface treatment processes are plasma processes, in which an ionized gas is applied to the surface of an article. Plasma gases and processing conditions are described more fully in U.S. Pat. Nos. 4,312,575 and 4,632,844, which are incorporated herein by reference. The plasma gas is preferably a mixture of lower alkanes and nitrogen, oxygen or an inert gas.

In a preferred embodiment, the lens is plasma treated in the presence of a mixture of (a) a $C_{1-6}$ alkane and (b) a gas selected from the group consisting of nitrogen, argon, oxygen, and mixtures thereof. In a more preferred embodiment, the lens is plasma treated in the presence of a mixture of methane and air.

An even more preferred class of surface treatment processes are layer-by-layer coating processes, in which lenses are exposed iteratively in an alternating fashion to a solution of a first polyionic material and a solution of a second polyionic material having charges opposite of the charges of the first polyionic material.

"LbL coating", as used herein, refers to a surface coating on an article, which is formed via a layer-by-layer ("LbL") coating process. In general, a LbL coating comprises a plurality of bilayers, preferably from 4 to 20 bilayers. Each bilayer includes one layer of a first polyionic material and one layer of a second polyionic material having charges opposite of the charges of the first polyionic material.

As used herein, a "polyionic material" refers to a polymeric material that has a plurality of charged groups, such as polyelectrolytes, p- and n-type doped conducting polymers. Polyionic materials include both polycationic (having positive charges) and polyanionic (having negative charges) materials.

A polycationic material used in the present invention can generally include any material known in the art to have a plurality of positively charged groups along a polymer chain. For instance, suitable examples of such polycationic materials can include, but are not limited to, poly(allylamine hydrochloride) (PAH), poly(ethyleneimine) (PEI), poly (vinylbenzyltriamethylamine) (PVBT), polyaniline (PAN or PANI) (p-type doped) [or sulphonated polyaniline], polypyrrole (PPY) (p-typed doped), and poly(pyridinium acetylene).

A polycationic material used in the present invention can also include polymeric quaternary ammonium compounds (polyquats). When polyquats are used in the coating of an ophthalmic lens, they may impart antimicrobial properties to the ophthalmic lens.

A polyanionic material used in the present invention can generally include any material known in the art to have a plurality of negatively charged groups along a polymer chain. For example, suitable polyanionic materials can include, but are not limited to, polymethacrylic acid (PMA), polyacrylic acid (PAA), poly(thiophene-3-acetic acid) (PTAA), poly(4-styrenesulfonic acid) (PSS), sodium poly (styrene sulfonate) (SPS) and poly(sodium styrene sulfonate) (PSSS).

The foregoing lists are intended to be exemplary, but clearly are not exhaustive. A person skill in the art, given the disclosure and teaching herein, would be able to select a number of other useful polyionic materials.

In order to alter various characteristics of the coating, such as thickness, the molecular weight of the polyionic materials can be varied. In particular, as the molecular weight is increased, the coating thickness generally increases. However, if the increase in molecular weight increase is too substantial, the difficulty in handling may also increase. As such, polyionic materials used in a process of the present invention will typically have a molecular weight $M_n$ of about 2,000 to about 150,000. In some embodiments, the molecular weight is about 5,000 to about 100,000, and in other embodiments, from about 75,000 to about 100,000.

In a preferred embodiment of the invention, an LbL coating is a lubricious coating comprising a capping layer of polyvinylpyrrolidone or at least one lubricious bilayer which is composed of one layer of the lubricious coating material and one layer of a polyionic material having charges opposite of the charges of the lubricious coating material.

A "capping layer", as used herein, refers to the last layer of a coating material which is applied onto the surface of a medical device.

A "lubricious coating" refers to a coating that can impart increased surface hydrophilicity and increased lubricity to an ophthalmic lens.

As used herein, "increased surface hydrophilicity" or "increased hydrophilicity" in reference to a coated ophthalmic lens means that the coated lens has a reduced averaged contact angle.

An "average contact angle" refers to a contact angle (measured by Sessile Drop method), which is obtained by averaging measurements of at least 3 individual ophthalmic lenses.

As used herein, "increased lubricity" in reference to a coated contact lens means that the coated contact lens has a reduced averaged value of coefficient of friction (hereinafter CoF) relative to a uncoated contact lens, wherein both coated and uncoated contact lenses are made of the same core material. CoF may be one of important parameters that may affect the on-eye movement and thereby the wearer's comfort. High CoF may increase the likelihood of damaging mechanically the ocular epithelia and/or may lead to ocular discomfort.

Examples of lubricious coating materials include, but are not limited to, alginates, poly(allylamine hydrochloride) polymers comprising lactone as modifier units (PAH lactone), hyaluronic acid and salts thereof, Starburst® polyamidoamine (PAMAM dendrimers (Aldrich), PAAm-co-PAA, chondroitin sulfate, chitosan, proteoglycans, proteoglycan mimics, and mixtures thereof.

Contact lenses having an lubricious coating may find particular use in extended-wear contact lenses. The lubricious coating may have a reduced adverse effects on the desirable bulk properties of the lens, such as oxygen permeability, ion permeability, and optical properties.

It has been discovered and disclosed in U.S. application Ser. No. 09/005,317 that complex and time-consuming pretreatment of a core material (medical device) is not required prior to binding of a polyionic material to the core material. By simply contacting a core material of a medical device, for example, a contact lens, with one or more solutions each containing one or more polyionic materials, a LbL coating can be formed on a medical device to modify the surface properties of the core material of the medical device. A LbL coating can be a single layer or a bilayer or multiple bilayers.

Application of a LbL coating may be accomplished in a number of ways as described in pending U.S. patent applications (application Ser. Nos. 09/005,317, 09/774,942, 09/775,104), herein incorporated by reference in their entireties. One coating process embodiment involves solely dip-coating and dip-rinsing steps. Another coating process embodiment involves solely spray-coating and spray-rinsing steps. However, a number of alternatives involves various combinations of spray- and dip-coating and rinsing steps may be designed by a person having ordinary skill in the art.

One dip-coating alternative involves the steps of applying a coating of a first polyionic material to a core material of a medical device by immersing said medical device in a first solution of a first polyionic material; rinsing the medical device by immersing the medical device in a rinsing solution; and, optionally, drying the medical device. This procedure can be repeated using a second polyionic material, with the second polyionic material having charges opposite of the charges of the first polyionic material, in order to form a polyionic bilayer. This bilayer formation process may be repeated a plurality of times in order to produce a thicker LbL coating. A preferred number of bilayers is about 5 to about 20 bilayers. While more than 20 bilayers are possible, it has been found that delamination may occur in LbL coatings having an excessive number of bilayers.

The immersion time for each of the coating and rinsing steps may vary depending on a number of factors. Preferably, immersion of the core material into the polyionic solution occurs over a period of about 1 to 30 minutes, more preferably about 2 to 20 minutes, and most preferably about 1 to 5 minutes. Rinsing may accomplished in one step, but a plurality of rinsing steps can be quite efficient.

Another embodiment of the coating process is a single dip-coating process as described in U.S. application Ser. No. 09/775,104, herein incorporated by reference in its entirety. Such single dip-coating process involves dipping a core material of a medical device in a solution containing a negatively charged polyionic material and a positively charged polyionic material in an amount such that the molar charge ratio of said solution is from about 3:1 to about 100:1. Multiple bilayers can be formed on a medical device by using this single dip-coating process.

Another embodiment of the coating process involves a series of spray coating techniques. The process generally includes the steps of applying a coating of a first polyionic material to a core material of a medical device with a first solution of a first polyionic material; rinsing the medical device by spraying the medical device with a rinsing solution; and optionally, drying the medical device. Similar to the dip-coating process, the spray-coating process may be repeated with a second polyionic material, with the second polyionic material having charges opposite of the charges of the first polyionic material.

The contacting of the medical device with solution, either polyionic material or rinsing solution, may occur by a variety of methods. For example, the medical device may be dipped into both solutions. One preferred alternative is to apply the solutions in an spray or mist form. Of course, various combinations may be envisioned, e.g., dipping the medical device in the polyionic material followed by spraying the rinsing solution.

The spray coating application may be accomplished via a number of method. For example, a conventional spray coating arrangement may be used, i.e., the liquid material is sprayed by application of fluid, which may or may not be at elevated pressure, through a reduced diameter nozzle which is directed towards the deposition target.

Preferably, a spraying process is selected from the group consisting of an air-assisted atomization and dispensing process, an ultrasonic-assisted atomization and dispensing process, a piezoelectric assisted atomization and dispensing process, an electromechanical jet printing process, an electromechanical jet printing process, a piezo-electric jet printing process, a piezo-electric with hydrostatic pressure jet printing process, and a thermal jet printing process; and a computer system capable of controlling the positioning of the dispensing head of the spraying device on the ophthalmic lens and dispensing the coating liquid. Those spraying coating processes are described in U.S. Application No. 60/312,199, herein incorporated by reference in its entirety.

In accordance with the present invention, polyionic material solutions can be prepared in a variety of ways. In particular, a polyionic solution of the present invention can be formed by dissolving the polyionic material(s) in water or any other solvent capable of dissolving the materials. When a solvent is used, any solvent that can allow the components within the solution to remain stable in water is suitable. For example, an alcohol-based solvent can be used. Suitable alcohols can include, but are not limited to, isopropyl alcohol, hexanol, ethanol, etc. It should be understood that other solvents commonly used in the art can also be suitably used in the present invention.

Whether dissolved in water or in a solvent, the concentration of a polyionic material in a solution of the present invention can generally vary depending on the particular materials being utilized, the desired coating thickness, and a number of other factors. However, it may be typical to formulate a relatively dilute aqueous solution of polyionic material. For example, a polyionic material concentration can be between about 0.001% to about 0.25% by weight, between about 0.005% to about 0.10% by weight, or between about 0.01% to about 0.05% by weight.

In general, the polyionic solutions mentioned above can be prepared by any method well known in the art for preparing solutions. For example, in one embodiment, a polyanionic solution can be prepared by dissolving a suitable amount of the polyanionic material, such as polyacrylic acid having a molecular weight of about 90,000, in water such that a solution having a certain concentration is formed. In one embodiment, the resulting solution is a 0.001M PAA solution. Once dissolved, the pH of the polyanionic solution can also be adjusted by adding a basic or acidic material. In the embodiment above, for example, a suitable amount of 1N hydrochloric acid (HCl) can be added to adjust the pH to 2.5.

Polycationic solutions can also be formed in a manner as described above. For example, in one embodiment, poly (allylamine hydrochloride) having a molecular weight of about 50,000 to about 65,000 can be dissolved in water to form a 0.001M PAH solution. Thereafter, the pH can also be adjusted to 2.5 by adding a suitable amount of hydrochloric acid.

In some embodiments of the present invention, it may be desirable to apply a solution containing both polyanionic and polycationic materials within a single solution. For example, a polyanionic solution can be formed as described above, and then mixed with a polycationic solution that is also formed as described above. In one embodiment, the solutions can then be mixed slowly to form the coating solution. The amount of each solution applied to the mix depends on the molar charge ratio desired. For example, if a 10:1 (polyanion:polycation) solution is desired, 1 part (by volume) of the PAH solution can be mixed into 10 parts of the PAA solution. After mixing, the solution can also be filtered if desired.

A medical device of the invention can also be made by first applying a LbL coating to a mold for making a medical device and then transfer-grafting the coating to the medical device made from the mold, in substantial accordance with the teachings of U.S. patent application (Ser. No. 09/774, 942), herein incorporated by reference in its entirety.

Methods of forming mold sections for cast-molding a contact lens are generally well known to those of ordinary skill in the art. The process of the present invention is not limited to any particular method of forming a mold. In fact, any method of forming a mold can be used in the present invention. However, for illustrative purposes, the following discussion has been provided as one embodiment of forming a mold on which a color image can be printed in accordance with the present invention.

In general, a mold comprises at least two mold sections (or portions) or mold halves, i.e. first and second mold halves. The first mold half defines a first optical surface and the second mold half defines a second optical surface. The first and second mold halves are configured to receive each other such that a contact lens forming cavity is formed between the first optical surface and the second optical surface. The first and second mold halves can be formed through various techniques, such as injection molding. These half sections can later be joined together such that a contact lens-forming cavity is formed therebetween. Thereafter, a contact lens can be formed within the contact lens-forming cavity using various processing techniques, such as ultraviolet curing.

Examples of suitable processes for forming the mold halves are disclosed in U.S. Pat. No. 4,444,711 to Schad; U.S. Pat. No. 4,460,534 to Boehm et al.; U.S. Pat. No. 5,843,346 to Morrill; and U.S. Pat. No. 5,894,002 to Boneberger et al., which are also incorporated herein by reference.

Virtually all materials known in the art for making molds can be used to make molds for making contact lenses. For example, polymeric materials, such as polyethylene, polypropylene, and PMMA can be used. Other materials that allow UV light transmission could be used, such as quartz glass.

Once a mold is formed, a coating can be applied onto the optical surface (inner surface) of one or both mold portions by using the above-described LbL deposition techniques. The inner surface of a mold portion is the cavity-forming surface of the mold and in direct contact with lens-forming material. A coating can be applied onto the mold portion defining the posterior (concave) surface of a contact lens or on the mold section defining the anterior surface of a contact lens or on both mold portions.

Once a coating is applied onto the optical surface of one or both mold portions, a polymer composition of the invnetion can then be dispensed into the contact lens forming cavity defined by the assembled mold halves. The lens material can then be cured, i.e. polymerized, within the contact lens-forming cavity to form the contact lens, whereby at least a portion of the transferable coating detaches from the optical surface and reattaches to the formed contact lens.

Any known method for curing a polymerizable composition can be used. Exemplary known methods for curing a polymerizable composition include, without limitation, thermal curing and photo curing methods.

The ophthalmic lenses of the present invention have special utility as extended-wear contact lenses. They may be continuously worn for long periods of time without substantial corneal swelling or wearer discomfort. The method of wear includes (a) applying the lens to the eye and (b) allowing the lens to remain in intimate contact with the eye and tear fluids for a period of at least 24 hours without substantial adverse impact on corneal health or wearer comfort.

A preferred method includes additional steps of (c) removing the lens from the ocular environment; (d) treating the lens (i.e., disinfecting or cleaning the lens); (e) re-applying the lens to the eye; and (f) allowing the lens to remain in intimate contact with the eye and tear fluids for a period of at least an additional 24 hours without substantial adverse impact on corneal health or wearer comfort.

In a preferred embodiment, the lens is worn for a continuous period of at least four (4) days without substantial corneal swelling or wearer discomfort. In another preferred embodiment, the lens is worn for a continuous period of at least seven (7) days without substantial corneal swelling or wearer discomfort.

The ophthalmic lens may be manufactured, generally, by thoroughly mixing the polymer composition of the present invention, applying an appropriate amount of the mixture to a lens mold cavity, and initiating polymerization. Photoinitiators, such as those commercially available photoinitiators, e.g., DAROCUR® 1173 (a photoinitiator available from Ciba-Geigy Corporation), may be added to the polymer composition to aid in initiating polymerization. Polymerization may be initiated by a number of well known techniques, which, depending on the polymerizable material, may include application of radiation such as microwave, thermal, e-beam and ultraviolet. A preferred method of initiating polymerization is by application of ultraviolet radiation.

The previous disclosure will enable one having ordinary skill in the art to practice the invention. In order to better enable the reader to understand specific embodiments and the advantages thereof, reference to the following examples is suggested. However, the following examples should not be read to limit the scope of the invention.

EXAMPLE 1

Synthesis of Macromers

Macromers with a structure shown in FIG. 1 are synthesized according to the following procedures in substantial accordance with teachings in Example B-1 to B-4 of U.S. Pat. No. 5,849,811.

(a)

51.5 g (50 mmol) of the perfluoropolyether Fomblin® ZDOL (from Ausimont S.p.A, Milan) having a mean molecular weight of 1030 g/mol and containing 1.96 meq/g of hydroxyl groups according to end-group titration is introduced into a three-neck flask together with 50 mg of dibutyltin dilaurate. The flask contents are evacuated to about 20 mbar with stirring and subsequently decompressed with argon. This operation is repeated twice. 22.2 g (0.1 mol) of freshly distilled isophorone diisocyanate kept under argon are subsequently added in a counterstream of argon. The temperature in the flask is kept below 30° C. by cooling with a waterbath. After stirring overnight at room temperature, the reaction is complete. Isocyanate titration gives an NCO content of 1.40 me q/g (theory: 1.35 meq/g).

202 g of the α,ω-hydroxypropyl-terminated polydimethylsiloxane KF-6001 from Shin-Etsu having a mean molecular weight of 2000 g/mol (1.00 meq/g of hydroxyl groups according to titration) are introduced into a flask. The flask contents are evacuated to approx. 0.1 mbar and decompressed with argon. This operation is repeated twice. The degassed siloxane is dissolved in 202 ml of freshly distilled toluene kept under argon, and 10 mg of dibutyltin dilaurate (DBTDL) are added. After complete homogenization of the solution, all the perfluoropolyether reacted with isophorone diisocyanate (IPDI) is added under argon. After stirring overnight at room temperature, the reaction is complete. The solvent is stripped off under a high vacuum at room temperature. Microtitration shows 0.36 meq/g of hydroxyl groups (theory 0.37 meq/g). 13.78 g (88.9 mmol) of 2-isocyanatoethyl methacrylate (IEM) are added under argon to 247 g of the α,σ-hydroxypropyl-terminated polysiloxane-perfluoropolyether-polysiloxane three-block copolymer (a three-block copolymer on stoichiometric average, but other block lengths are also present). The mixture is stirred at room temperature for three days. Microtitration then no longer shows any isocyanate groups (detection limit 0.01 meq/g). 0.34 meq/g of methacryl groups are found (theory 0.34 meq/g).

The macromer prepared in this way is completely colourless and clear. It can be stored in air at room temperature for several months in the absence of light without any change in molecular weight.

(b)

The first step of the macromer synthesis described under procedure (a) is repeated. An isocyanate titration of the perfluoropolyether reacted with IPDI gives a content of 1.33 meq/g of NCO (theory 1.35 meq/g).

In a second step, 87.1 g of the α,σ-hydroxypropyl-terminated polydimethylsiloxane TegomerH-Si2111 (Th. Goldschmidt AG, Essen) having a mean molecular weight of 890 g/mol (2.25 meq/g of hydroxyl groups according to titration) are dissolved in 87 ml of toluene. After the reaction has been carried out as indicated under procedure (a) and the solvent has been removed, a hydroxyl group content of 0.66 meq/g is determined by microtitration (theory 0.60 meq/g). The resultant intermediate is in turn reacted with a stoichiometric amount of isocyanatoethyl methacrylate. Microtitration then no longer shows any isocyanate groups (detection limit 0.01 meq/g). 0.56 meq/g of methacryl groups are found (theory 0.53 meq/g). The macromer prepared in this way is completely colourless and clear and has a long shelf life.

(c)

The first step of the macromer synthesis described under procedure (a) is repeated, but using a different perfluoropolyether: Fomblin® ZDOLTX (from Ausimont S.p.A., Milan). This material is terminated by O—$CF_2$—$CH_2$—$(OCH_2CH_2)_n$—OH (where n=0, 1 or 2). The material used has a mean molecular weight of 1146 g/mol, and contains 1.72 meq/g of hydroxyl groups according to end-group analysis. An isocyanate titration of the perfluoropolyether reacted with IPDI shows a content of 1.23 meq/g of NCO (theory 1.25 meq/g).

In the second step, a stoichiometric amount of Tegomer Hi-Si2111 and toluene are again added. After the reaction has been carried out as indicated under procedure (a) and the solvent has been removed, a hydroxyl group content of 0.63 meq/g is determined by microtitration (theory 0.58 meq/g). The resultant intermediate is in turn reacted with a stoichiometric amount of isocyanatoethyl methacrylate. Microtitration then no longer shows any isocyanate groups (detection limit 0.01 meq/g). 0.55 meq/g of methacryl groups are found (theory 0.51 meq/g). The macromer prepared in this way is completely colourless and clear and has a long shelf life.

(d)

The first step of the macromer synthesis described under procedure (a) is repeated, but 5.0 g of Fomblin/ZDOL and 2.18 g of IPDI are employed. When the reaction is complete, microtitration shows an isocyanate group content of 1.31 meq/g of hydroxyl groups (theory 1.36 meq/g).

The second step of the synthesis described under procedure (a) is likewise carried out analogously, the stoichiometric ratio between isocyanate-terminated perfluoropolyether and hydroxypropyl-terminated polysiloxane being 2:3. After the reaction has been completed and the solvent has been removed, microtitration shows a content of 0.2 meq/g of hydroxyl groups (theory 0.18 meq/g).

The third step of the synthesis described under procedure (a) is likewise carried out analogously, IEM being employed in a precisely stoichiometric ratio. After the reaction, free isocyanate groups can no longer be detected (detection limit 0.01 meq/g). 0.19 meq/g of methacryl groups are found (theory 0.19 meq/g).

Production of Contact Lenses 25.92 g of the macromer prepared from procedure (a) are added to a clean container. 19.25 g of 3-tris(trimethylsiloxy) silylpropyl methacrylate (TRIS from Shin-Etsu, product No. KF-2801) are added, followed by 1.00 gm of photoinitiator Darocur® 1173 (Ciba). 28.88 g dimethylacrylamide (DMA) are added, followed by 24.95 g of ethanol. After complete homogenization of the solution, this solution is filtered through a Teflon membrane having a pore width of 0.5 microns under nitrogen or air pressure. This solution is then pipetted into dust-free contact-lens moulds made from polypropylene. The moulds are closed, and the polymerization reaction is effected by UV irradiation (5.0 mW/cm2, 30 min.), with simultaneous crosslinking. The moulds are then opened and placed in isopropanol, causing the resultant lenses to swell out of the moulds. The lenses are extracted for 4 hours minimum with 100% isopropyl alcohol before being placed into water. The lenses are coated and finally equilibrated in phosphate-buffered physiological saline solution in specially designed foil packages and then autoclaved at 120° C. for 30 minutes. All physical data measurements are carried out on autoclaved lenses.

LbL Coatings

Once equilibrated, the lenses are transferred into a series of layer-by-layer (LbL) tanks for coating application. The tanks are a series of tanks containing alternating solutions of PAA and PAH respectively. Lenses are dipped and circulated in a PAA solution first for a defined time minimum followed by alternating dipping in PAH dominant solutions and PAA dominant solutions.

Physical Properties of the Lens Materials

TABLE I

Physical properties of polymer materials

| Water Content [%] | Ionoflux Diffusion Coefficient (mm²/min) | DK [barrers] | Modulus of Elasticity [MPa] | Refractive Index |
|---|---|---|---|---|
| 33 ± 2% | 6.90 × 10⁻³–8.44 × 10⁻³ | 57–86 | 1.0 | 1.42 ± 0.12 |

What is claimed is:

1. An ophthalmic lens, comprising a core polymeric material and an ophthalmically compatible surface which is more hydrophilic than said core polymeric material, wherein the ophthalmic lens has a high oxygen permeability characterized by a $D_k$ greater than 56 barrers and a high ion permeability characterized by an ionoflux diffusion coefficient of great than $4.0 \times 10^{-4}$ mm 2/min and comprises a water content of at least 25 weight percent when fully hydrated, wherein said ophthalmically compatible surface is an LbL coating comprisisg a plurality of bilayers and a capping layer of polyvinylpyrrolidone, wherein each bilayer comprises one layer of a first polyionic material and one layer of a second polyionic material having charges opposite of the charges of the first polyionic materials, wherein said core polymeric material is prepared by curing in a mold in an oxygen-containing or oxygen-free atmosphere a polymer composition including:

(i) about 5 to about 40 weight percent of a macromer, wherein said macromer is selected from the group consisting of Macromer A, Macromer B, Macromer C, and Macromer D;

(ii) about 10 to about 30 weight percent of a siloxane-containing monomer; and (iii) about 30 to about 50 weight percent of a hydrophilic monomer, wherein said weight percentages are based upon the dry weight of the polymer components, wherein Macromer A is a polysiloxane macromer having a number-average molecular weight of 2000 to 10,000 and the the segment of the formula:

CP-PAO-DU-ALK-PDMS-ALK-DU-PAO-CP where PDMS is a divalent poly(disubstituted siloxane), ALK is an alkylene or alkylenoxy group having at least 3 carbon atoms, DU is a diurethane-containing group, PAO is a divalent polyoxyalkylene, and CP is selected from acrylates and methacrylates, wherein Macromer B is a polysiloxane-comprising perfluoroalkyl ether and has the formula:

$P_1\text{-}(Y)_m\text{-}(L\text{-}X_1)p\text{-}Q\text{-}(X_1\text{-}L)_p\text{-}(Y)_m\text{-}P_1$ where each $P_1$, independently of the others, is a free-radical-polymerizable group; each Y, independently of the others, is —CONHCOO—, —CONHCONH—, —OCONHCO—, —NHCONHCO—, —NHCO—, —CONH—, —NHCONH—, —COO—, —OCO—, —NHCOO— or —OCONH—; m and p, independently of one another, are 0 or 1; each L, independently of the others, is a divalent radical of an organic compound having up to 20 carbon atoms; each $X_1$, independently of the others, is —NHCO—, —CONH—, —NHCONH—, —COO—, —OCO—, —NHCOO— or —OCONH—; and Q is a bivalent polymer fragment consisting of the segments:

-(E)$_k$-Z-CF$_2$—(OCF$_2$)$_x$—(OCF$_2$CF$_2$)$_y$—OCF$_2$-Z-(E)$_k$-,  (a)

where x+y is a number in the range of from 10 to 30; each Z, independently of the others, is a divalent radical having up to 12 carbon atoms or Z is a bond;

each E, independently of the others, is —(OCH$_2$CH$_2$)$_q$—, where q has a value of from 0 to 2, and where the link -Z-E- represents the sequence -Z-(OCH$_2$CH$_2$)$_q$—; and k is 0 or 1;

(b)

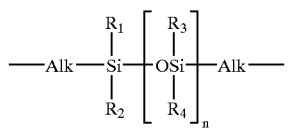

wherein is an integer from 5 to 100; Alk is alkylene having up to 20 carbon atoms; 80–100% of the radicals $R_1$, $R_2$, $R_3$ and $R_4$, independently of one another, are alkyl and 0–20% of the radicals $R_1$, $R_2$, $R_3$ and $R_4$, independently of one another, are alkenyl, aryl or cyanoalkyl; and (c) $X_2$—R—$X_2$, where R is a divalent organic radical having up to 20 carbon atoms, and each $X_2$, independently of the others, is —NHCO—, —CONH—, —NHCONH—, —COO—, —OCO—, —NHCOO— or OCONH—;

with the provisos that there must be at least one of each segment (a), (b), and (c) in Q, that each segment (a) or (b) has a segment (c) attached to it, and that each segment (c) has a segment (a) or (b) attached to it;

wherein Macromer C has an average molecular weight of from about 300 to about 30,000 and comprises at least one segment of the formula (I), (IV), (V), (VI) or (VII):

  (I)

  (IV)

  (V)

  (VI)

  (VII)

in which (a) is a polysiloxane segment; (b) is a polyol segment which contains at least 4 carbon atoms; Z is a segment (c) or a group $X_1$; (c) is defined as $X_2$—R—$X_2$, wherein R is a bivalent radical of an organic compound having up to 20 carbon atoms and each $X_2$ independently of the other is a bivalent radical which contains at least one carbonyl group; $X_1$ is defined as $X_2$; x is 0, 1 or 2; q has an average numerical value of 1–20; and (d) is a radical of the formula (II):

$X_3\text{-L-}(Y)_k\text{-}P_1$  (II)

in which $P_1$ is alkenyl, alkenylaryl or alkenylarylenealkyl having up to 20 carbon atoms; Y and $X_3$ independently of one another are a bivalent radical which contains at least one carbonyl group; k is 0 or 1; and L is a bond or a divalent radical having up to 20 carbon atoms of an organic compound, wherein the polysiloxane segment (a) is derived from a compound containing at least one primary amino or hydroxyl group and being of the formula (III):

  (III)

in which n is an integer from 5 to 500; 99.8–25% of the radicals $R_1$, $R_2$, $R_3$, $R_4$, $R_5$ and $R_6$ independently of one another are alkyl and 0.2–75% of the radicals $R_1$, $R_2$, $R_3$, $R_4$, $R_5$ and $R_6$ independently of one another are partly fluorinated alkyl, aminoalkyl, alkenyl, aryl, cyanoalkyl, alk-NH-alk-NH$_2$ or alk-(OCH$_2$)$_m$—(OCH$_2$)p-OR$_7$, $R_7$ is hydrogen or lower alkyl, alk is alkylene, and m and p independently of one another are an integer from 0 to 10, wherein the alkylenoxy groups —(OCH$_2$CH$_2$)$_m$ and —(OCH$_2$)$_p$ in formula (III) are either distributed randomly in a ligand alk-(OCH$_2$CH$_2$)$_m$—(OCH$_2$)$_p$-OR$_7$ or are distributed as blocks in a chain, wherein the polysiloxane segment (a) in formula (I) is linked a total of 1–50 times, via a group Z with the segment (b) or another segment (a), Z in an a-Z-a sequence always being a segment (c), wherein the segments (b) in Macromer C according to the formula (VI) are linked in total (per molecule) with up to 20 with up to 6 polymerizable segments (d), wherein the average number of segments (d) per molecule of the formula (VII) is in the range from 2 to 5, wherein macromer D has the formula:

ACRYLATE-LINK-ALK-O-ALK-PDAS-ALK-O-ALK-LINK-ACRYLATE in which the ACRYLATE is selected from acrylates and methacrylates; LINK is selected from urethanes and dirurethane linkages; ALK-O-ALK is R$_1$—O—R$_2$ or R$_3$—O—R$_4$, R$_1$, R$_2$, R$_3$, and R$_4$, independently of one another, are lower alkylene; and PDAS is a poly (dialkylsiloxane) having a segment of the formula:

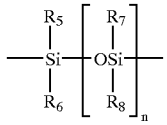

in which n is an integer from about 5 to about 500; and R$_5$, R$_6$, R$_7$, and R$_8$ are, independently of one another, are lower alkyl.

2. An ophthalmic lens of claim 1, wherein said ophthalmic lens is selected from the group consisting of contact lenses for vision correction, contact lenses for eye color modification, ophthalmic drug delivery devices, and ophthalmic wound healing devices.

3. An ophthalmic lens of claim 2, wherein said ophthalmic lens is a contact lens.

4. A contact lens of claim 3, wherein said contact lens further has: (1) a tensile modulus of less than about 1.5 Mpa; and/or (2) a short relaxation time constant (t$_1$) greater than about 3.5 seconds.

5. A contact lens of claim 3, wherein said contact lens further has a Hydrodell Water Permeability Coefficient of greater than about 0.2×10$^{-6}$ cm$^2$/min.

6. A contact lens of claim 3, wherein said core polymeric material comprises at least a color additive.

7. A contact lens of claim 6, wherein said color additive is copper phthalocyanine.

8. A contact lens of claim 1, wherein said LbL coating comprises at least one lubricious bilayer which is composed of one layer of a lubricious coating material and one layer of a polyionic material having charges opposite of the charges of the lubricious coating material, wherein the lubricious coating material is selected from the group consisting of alginates, poly(allylamine hydrochloride) polymers comprising lactone as modifier units, hyaluronic acid and salts thereof, PAMAM dendrimers, PAAm-co-PAA, chondroitin sulfate, chitosan, proteoglycans, mimics, and mixtures thereof.

9. A contact lens of claim 1, wherein said LbL coating includes about 5 to 20 bilayers.

10. A contact lens of claim 9, wherein said first polyionic material is a polycationic material and said second polyionic material is a polyanionic material.

11. A contact lens of claim 10, wherein said polycationic material polycationic materials is selected from the group consisting of poly(allylamine hydrochloride) (PAH), poly (ethyleneimine) (PEI), poly(vinylbenzyltriamethylamine) (PVBT), polyaniline, sulphonated polyaniline, polypyrrole, and poly(pyridinium acetylene).

12. A contact lens of claim 10, wherein said polyanionic material is selected from the group consisting of poly-methacrylic acid (PMA), polyacrylic acid (PAA), poly (thiophene-3-acetic acid) (PTAA), poly(4-styrenesulfonic acid) (PSS), sodium poly(styrene sulfonate) (SPS) and poly (sodium styrene sulfonate) (PSSS).

13. A method for making an ophthalmic lens, comprising the steps of:

(1) curing a polymer composition in a mold in an oxygen-containing or oxygen-free atmosphere to obtain a core of the ophthalmic lens, wherein the polymer composition includes:

(I) about 5 to about 40 weight percent of a macromer, wherein said macromer is selected from the group consisting of Macromer A, Macromer B, Macromer C, and Macromer D;

(II) about 10 to about 30 weight percent of a siloxane-containing monomer; and (III) about 30 to about 50 weight percent of a hydrophilic monomer, wherein said weight percentages are based upon the dry weight of the polymer components, wherein Macromer A is a polysiloxane macromer having a number-average molecular weight of 2000 to 10,000 and the the segment of the formula:

CP-PAO-DU-ALK-PDMS-ALK-DU-PAO-CP where PDMS is a divalent poly(disubstituted siloxane), ALK is an alkylene or alkylenoxy group having at least 3 carbon atoms, DU is a diurethane-containing group, PAO is a divalent polyoxyalkylene, and CP is selected from acrylates and methacrylates, wherein Macromer B is a polysiloxane-comprising perfluoroalkyl ether and has the formula:

P$_1$-(Y)$_m$-(L-X$_1$)p-Q-(X$_1$-L)$_p$-(Y)$_m$-P$_1$ where each P$_1$, independently of the others, is a free-radical-polymerizable group; each Y, independently of the others, is —CONHCOO—, —CONHCONH—, —OCONHCO—, —NHCONHCO—, —NHCO—, —CONH—, —NHCONH—, —COO—, —OCO—, —NHCOO— or —OCONH—; m and p, independently of one another, are 0 or 1; each L, independently of the others, is a divalent radical of an organic compound having up to 20 carbon atoms; each X$_1$, independently of the others, is —NHCO—, —CONH—, —NHCONH—, —COO—, —OCO—, —NHCOO— or —OCONH—; and Q is a bivalent polymer fragment consisting of the segments:

-(E)$_k$-Z-CF$_2$—(OCF$_2$)$_x$—(OCF$_2$CF$_2$)$_y$—OCF$_2$-Z-(E)$_k$-,  (a)

where x+y is a number in the range of from 10 to 30;

each Z, independently of the others, is a divalent radical having up to 12 carbon atoms or Z is a bond;

each E, independently of the others, is —(OCH$_2$CH$_2$)$_q$—, where q has a value of from 0 to 2, and where the link -Z-E- represents the sequence -Z-(OCH$_2$CH$_2$)$_q$—; and k is 0 or 1;

(b)

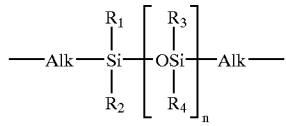

wheren is an integer from 5 to 100; Alk is alkylene having up to 20 carbon atoms; 80–100% of the radicals R$_1$, R$_2$, R$_3$ and R$_4$, independently of one another, are alkyl and 0–20% of the radicals R$_1$, R$_2$, R$_3$ and R$_4$, independently of one another, are alkenyl, aryl or cyanoalkyl; and (c) X$_2$—R—X$_2$, where R is a divalent organic radical having up to 20 carbon atoms, and each X$_2$, independently of the others, is —NHCO—, —CONH—, —NHCONH—, —COO—, —OCO—, —NHCOO— or OCONH—;

with the provisos that there must be at least one of each segment (a), (b), and (c) in Q, that each segment (a) or (b) has a segment (c) attached to it, and that each segment (c) has a segment (a) or (b) attached to it;

wherein Macromer C has an average molecular weight of from about 300 to about 30,000 and comprises at least one segment of the formula (I), (IV), (V), (VI) or (VII):

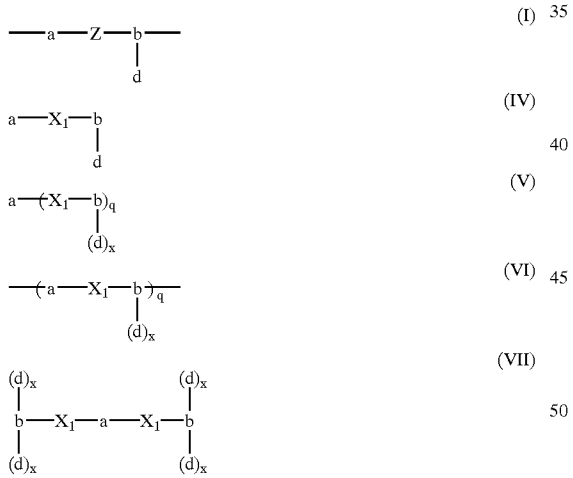

in which (a) is a polysiloxane segment; (b) is a polyol segment which contains at least 4 carbon atoms; Z is a segment (c) or a group X$_1$; (c) is defined as X$_2$—R—X$_2$, wherein R is a bivalent radical of an organic compound having up to 20 carbon atoms and each X$_2$ independently of the other is a bivalent radical which contains at least one carbonyl group; X$_1$ is defined as X$_2$; x is 0, 1 or 2; q has an average numerical value of 1–20; and (d) is a radical of the formula (II):

X$_3$-L-(Y)$_k$-P$_1$ (II)

in which P$_1$ is alkenyl, alkenylaryl or alkenylarylencalkyl having up to 20 carbon atoms; Y and X$_3$ independently of one another are a bivalent radical which contains at least one carbonyl group; k is 0 or 1; and L is a bond or a divalent radical having up to 20 carbon atoms of an organic compound, wherein the polysiloxane segment (a) is derived from a compound containing at least one primary amino or hydroxyl group and being of the formula (III):

in which n is an integer from 5 to 500; 99.8–25% of the radicals R$_1$, R$_2$, R$_3$, R$_4$, R$_5$ and R$_6$ independently of one another are alkyl and 0.2–75% of the radicals R$_1$, R$_2$, R$_3$, R$_4$, R$_5$ and R$_6$ independently of one another are partly fluorinated alkyl, aminoalkyl, alkenyl, aryl, cyanoalkyl, alk-NH-alk-NH$_2$ or alk-(OCH$_2$)$_m$—(OCH$_2$)p-OR$_7$, R$_7$ is hydrogen or lower alkyl, alk is alkylene, and m and p independently of one another are an integer from 0 to 10, wherein the alkylenoxy groups —(OCH$_2$CH$_2$)$_m$ and —(OCH$_2$)$_p$ in formula (III) are either distributed randomly in a ligand alk-(OCH$_2$CH$_2$)$_m$—(OCH$_2$)$_p$—OR$_7$ or are distributed as blocks in a chain, wherein the polysiloxane segment (a) in formula (I) is linked a total of 1–50 times, via a group Z with the segment (b) or another segment (a), Z in an a-Z-a sequence always being a segment (c), wherein the segments (b) in Macromer C according to the formula (VI) are linked in total (per molecule) with up to 20 with up to 6 polymerizable segments (d), wherein the average number of segments (d) per molecule of the formula (VII) is in the range from 2 to 5, wherein macromer D has the formula:

ACRYLATE-LINK-ALK-O-ALK-PDAS-ALK-O-ALK-LINK-ACRYLATE in which the ACRYLATE is selected from acrylates and methacrylates; LINK is selected from urethanes and dirurethane linkages; ALK-O-ALK is R$_1$—O—R$_2$ or R$_3$—O—R$_4$, R$_1$, R$_2$, R$_3$, and R$_4$, independently of one another, are lower alkylene; and PDAS is a poly(dialkylsiloxane) having a segment of the formula:

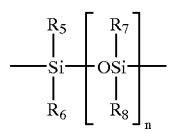

in which n is an integer from about 5 to about 500; and R$_5$, R$_6$, R$_7$, and R$_8$ are, independently of one another, are lower alkyl;

(2) applying a hydrophilic coating onto the surface of said core via a LbL coating process to obtain an LbL coating comprising a plurality of bilayers and a capping layer of polyvinylpyrrolidone, wherein each bilayer comprises one lever of a first polyionic material and one layer of a second polyionic material having charges opposite of the charges of the first polyionic materials, wherein the ophthalmic lens has a high oxygen permeability characterized by a Dk greater than 56 barrers and a high ion permeability characterized by an ionoflux diffusion coefficient of great than $6.0 \times 10^{-4}$ mm$^2$/min and comprises a water content of at least 25 weight percent when fully hydrated.

14. A method of claim 13, wherein said hydrophilic monomer is selected from the group consisting of hydroxyl-substituted lower alkyl (C$_1$ to C$_8$) acrylates and methacrylates, acrylamide, methacrylamide, (lower allyl) acrylamides and -methacrylamides, ethoxylated acrylates and methaerylates, hydroxyl-substituted (lower alkyl) acrylamides and -methacrylamides, hydroxyl-substituted lower alkyl vinyl ethers, sodium vinylsulfonate, sodium styrenesulfonate, 2-acrylamido-2-methylpropanesulfonic acid, N-vinylpyrrole, N-vinyl-2-pyrrolidone, 2-vinyloxazoline, 2-vinyl-4,4'-dialkyloxazolin-5-one, 2- and 4-vinylpyridine, vinylically unsaturated carboxylic acids having a total of 3 to 5 carbon atoms, amino(lower alkyl)-, mono(lower alkylamino)(lower alkyl) and di(lower alkylamino)(lower alkyl)acrylates and methaerylates, and allyl alcohol.

15. A method of claim 14, wherein said hydrophilic monomer is 2-hydroxyethylmethacrylate (HEMA), hydroxyethyl acrylate, hydroxypropyl acrylate, hydroxypropyl methacrylate (HPMA), trimethylammonium 2-hydroxy propylmethacrylate hydrochloride, dimethylaminoethyl methacrylate (DMAEMA), dimethylaminoethylmethacrylamide, aerylamide, methacrylamide, allyl alcohol, vinylpyridine, glycerol methacrylate, N-(1,1dimethyl-3-oxobutyl)acrylamide, N-vinyl-2-pyrrolidone (NVP), acrylic acid, methacrylic acid, or N,N-dimethyacrylamide (DMA).

16. A method of claim 15, wherein said siloxane-containing monomer is 3-methaeryloxypropyltris (trimethylsiloxy) silane (TRIS).

17. A method of claim 15, wherein the polymer composition further comprises an amount of less than about 3% weight percent of a photoinitiator.

18. A method of claim 17, wherein said photoinitiator is 2-hydroxy-2-methyl-1-phenyl-1-propanone.

19. A method of claim 15, wherein the polymer composition further comprising an amount of less than about 10% weight percent of a crosslinking agent.

20. A method of claim 19, wherein said crosslinking agent is selected from the group consisting of allyl(meth)acrylate, lower alkylene glycol di(meth)acrylate, poly lower alkylene glycol di(meth)acrylate, lower alkylene di(meth)acrylate, divinyl ether, divinyl sulfone, di- or trivinylbenzene, trimethylolpropane tri(meth)acrylate, pentaerythritol tetra(meth)acrylate, bisphenol A di(meth)acrylate, methylenebis(meth)acrylamide, triallyl phthalate and diallyl phthalate.

21. A method of claim 20, wherein said crosslinking agent is ethylene glycol dimethacrylate (EGDMA).

22. A method of claim 15, wherein the polymer composition further comprises a solvent which is selected from the group consisting of water, C$_1$-C$_4$ alkanols, dimethylformamide, dimethyl sulfoxide, methyl ethyl ketone, acteone, cyclohexanone, toluene, ethers, THF, dimethoxyethane, dioxane, and trichloroethane, and mixtures thereof.

23. A method of claim 22, wherein said solvent is ethanol and present in an amount of from about 15 to about 40 weight percent.

24. A method of claim 15, wherein said siloxane-containing monomer is 3-methacryloxypropyltris (trimethylsiloxy) silane (TRIS), wherein said hydrophilic monomer is N,N-Dimetryl acrylamide.

25. A method of claim 15, wherein the polymer composition futher comprises a color additive.

26. A method of claim 25, wherein the color additive is copper phthalocyanine.

27. A method of claim 15, wherein the LbL coating comprises at least one lubricious bilayer which is composed of one layer of a lubricious coating material and one layer of a polyionic material having charges opposite of the charges of the lubricious coating material, wherein the lubricious coating material is selected from the group consisting of alginates, poly(allylamine hydrochloride) polymers comprising lactone as modifier units, hyaluronic acid and salts thereof, polyamidoamine dendrimers, chondroitin sulfate, chitosan, proteoglycans, and mixtures thereof.

* * * * *